(12) United States Patent
Sinnott et al.

(10) Patent No.: US 6,508,789 B1
(45) Date of Patent: Jan. 21, 2003

(54) SYSTEMS AND METHODS FOR COUPLING A DRAINAGE CATHETER TO A PATIENT AND DECOUPLING THE DRAINAGE CATHETER FROM THE PATIENT

(75) Inventors: Margaret Mary Sinnott, Logan, UT (US); Arlin Dale Nelson, Sandy, UT (US); John Heber Whiting, Jr., Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 81 days.

(21) Appl. No.: 09/586,635

(22) Filed: Jun. 5, 2000

(51) Int. Cl.[7] ............................................. A61M 5/178
(52) U.S. Cl. ........................... 604/164.02; 604/164.01; 604/95.01; 604/95.04; 604/95.05; 604/264; 604/170.03; 600/285
(58) Field of Search ................... 604/164.02, 164.01, 604/95.01, 95.04, 95.05, 264, 9, 8, 280, 170.03, 533, 523, 905; 600/585

(56) References Cited

U.S. PATENT DOCUMENTS

| | | | |
|---|---|---|---|
| 1,207,479 A | 12/1916 | Bisgaard | 604/95.01 |
| 3,119,392 A | 1/1964 | Zeiss | 604/95.04 |
| 3,394,954 A | 7/1968 | Sarns | 604/905 |
| 3,554,580 A | 1/1971 | Goyke | 604/533 |
| 3,924,633 A | 12/1975 | Cook | 604/95.04 |
| 4,586,923 A | 5/1986 | Gould | 604/95.04 |
| 4,592,749 A | 6/1986 | Ebling | 604/533 |
| 4,643,720 A | 2/1987 | Lanciano | 604/95.04 |
| 4,661,300 A | 4/1987 | Daugherty | |
| 4,740,195 A | 4/1988 | Lanciano | 604/95.04 |
| 4,787,892 A | 11/1988 | Rosenberg | 604/170.02 |
| 4,846,175 A | 7/1989 | Frimberger | |
| 4,869,719 A | 9/1989 | Hogan | |
| 4,963,129 A | 10/1990 | Rusch | 604/8 |
| 4,969,879 A | 11/1990 | Lichte | 604/533 |
| 4,986,814 A * | 1/1991 | Burney et al. | 604/264 |

(List continued on next page.)

FOREIGN PATENT DOCUMENTS

| | | | |
|---|---|---|---|
| DE | 35 25 165 A1 * | 1/1987 | |
| WO | WO 94/23776 | 10/1994 | 604/164.01 |
| WO | WO 96/34560 | 11/1996 | |

OTHER PUBLICATIONS

Castañeda–Zúñiga, M.D., M.Sc., et al., Interventional Radiology, vol. 2, Third Edition; Copyright ©1997 Williams & Wilkins; pp. 1049–1147, 1150–1269, 1446–1512, and 1745–1783.

(List continued on next page.)

Primary Examiner—Thomas Denion
Assistant Examiner—Thai-Ba Trieu
(74) Attorney, Agent, or Firm—Workman, Nydegger & Seeley

(57) ABSTRACT

Systems and methods for coupling a catheter, such as a drainage catheter, to a patient's body and decoupling the catheter from the body are disclosed. Embodiments of the present invention take advantage of the flexibility of a catheter cannula and allow for a self-contained system that secures the catheter cannula within the body while bodily fluid is draining. In one embodiment, the catheter is coupled to the body by compressing a proximal hub member to a distal hub member, causing the cannula to curl and form an anchoring configuration (i.e. a loop, pigtail, j-curve, malecot, etc.). In compressing the portions, one or more fingers within the proximal hub member force a cord into one or more corresponding channels within the distal hub member, thereby shortening the amount of cord in the cannula. The proximal and distal hub members can be locked together in the compressed position for as long as the catheter is to be coupled to the body. The catheter can be decoupled from the patient's body by returning the hub to an extended position, pulling on the cord, or removing a wire to release the cord and allow for removal of the catheter cannula from the body.

15 Claims, 16 Drawing Sheets

U.S. PATENT DOCUMENTS

| | | | | |
|---|---|---|---|---|
| 5,030,204 | A | 7/1991 | Badger et al. | 604/95.04 |
| 5,041,085 | A | 8/1991 | Osborne et al. | 604/95.05 |
| 5,052,998 | A | 10/1991 | Zimmon | 604/8 |
| 5,078,684 | A | 1/1992 | Yasuda | 604/95.05 |
| 5,078,701 | A | 1/1992 | Grassi | 604/264 |
| 5,185,004 | A | 2/1993 | Lashinski | 604/95.04 |
| 5,213,575 | A | 5/1993 | Scotti | 604/95.05 |
| 5,300,045 | A | 4/1994 | Plassche | 604/164.01 |
| 5,308,318 | A | 5/1994 | Plassche | 604/540 |
| 5,318,576 | A | 6/1994 | Plassche | |
| 5,352,198 | A | 10/1994 | Goldenberg | 604/95.04 |
| 5,380,270 | A | 1/1995 | Ahmadzadeh | 604/9 |
| 5,399,165 | A | 3/1995 | Paul, Jr. | 604/95.04 |
| 5,419,764 | A | 5/1995 | Roll | 604/95.04 |
| 5,472,435 | A | 12/1995 | Sutton | 604/540 |
| 5,489,269 | A | 2/1996 | Aldrich | 604/95.04 |
| 5,522,400 | A | 6/1996 | Williams | 604/264 |
| 5,666,970 | A | 9/1997 | Smith | 128/772 |
| 5,704,926 | A | 1/1998 | Sutton | 604/95.01 |
| 5,730,724 | A | 3/1998 | Plishka et al. | 604/95.04 |
| 5,733,248 | A * | 3/1998 | Adams et al. | 600/585 |
| 5,765,568 | A | 6/1998 | Sweezer | |
| 5,928,208 | A | 7/1999 | Chu | 604/280 |
| 5,941,849 | A * | 8/1999 | Amos et al. | 604/95.04 |
| 5,989,241 | A | 11/1999 | Plishka et al. | 604/540 |
| 6,042,577 | A | 3/2000 | Chu et al. | 604/523 |
| 6,231,542 | B1 * | 5/2001 | Amos et al. | 604/95.01 |
| 2002/0029013 | A1 * | 3/2002 | Paskar | 604/95.01 |

OTHER PUBLICATIONS

Braun, Michael A., et al., "Interventional Radiology Procedure Manual," © Churchill Livingstone, Inc., 1997; pp. 193–206 and 229–250.

"Medi–Tech Biliary Drainage Products," pp. 6–1 through 6–5 (to the best of Applicants' knowledge and belief, this reference was published at least as early as Jun. 4, 2000.

Press Release, Nov. 24, 1999, Annual Meeting of the Radiological Society of North America, Angiodynamics Introduces New LIne of Drainage Catheters, 2 pages.

AngioDynamics, Incorporated, Ordering Information Brochure for ABSCESSION Drainage Catheter, MLC 093 Rev A 11/99.

* cited by examiner

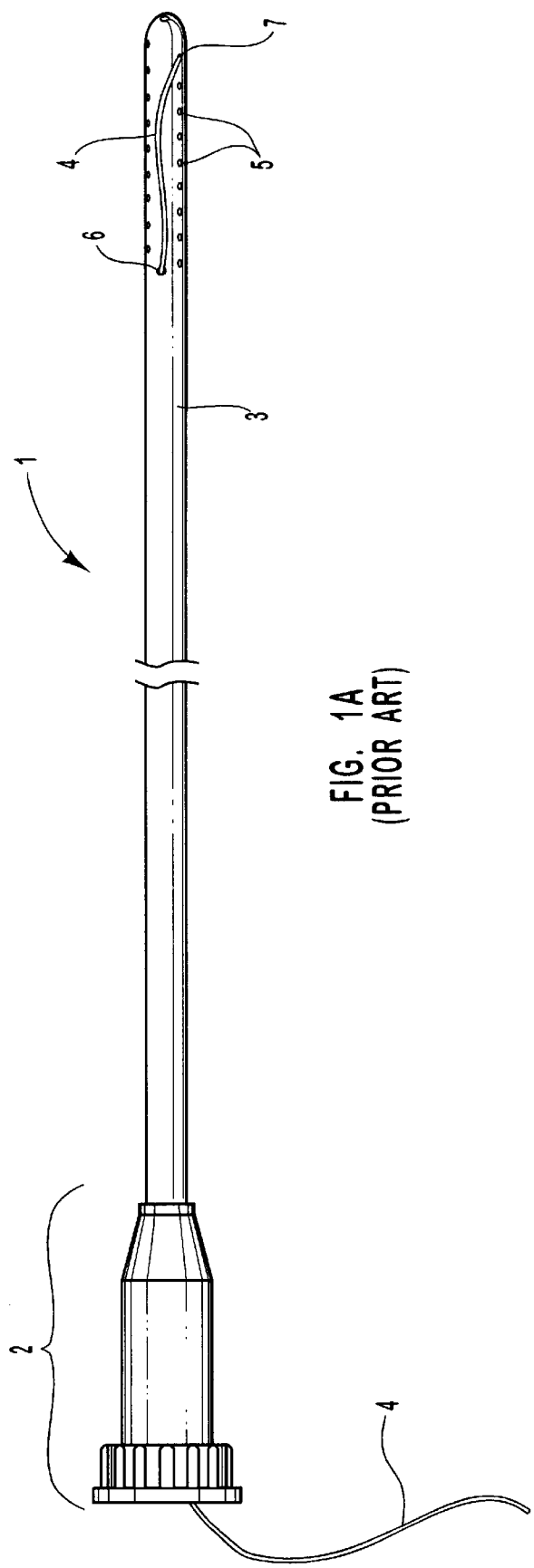
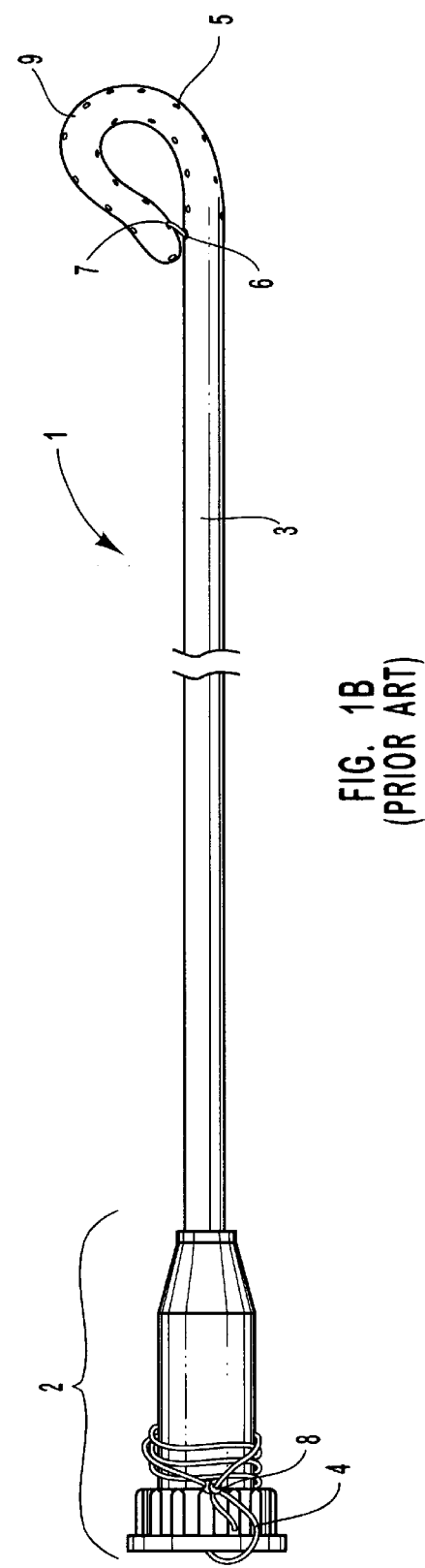
FIG. 1A (PRIOR ART)
FIG. 1B (PRIOR ART)

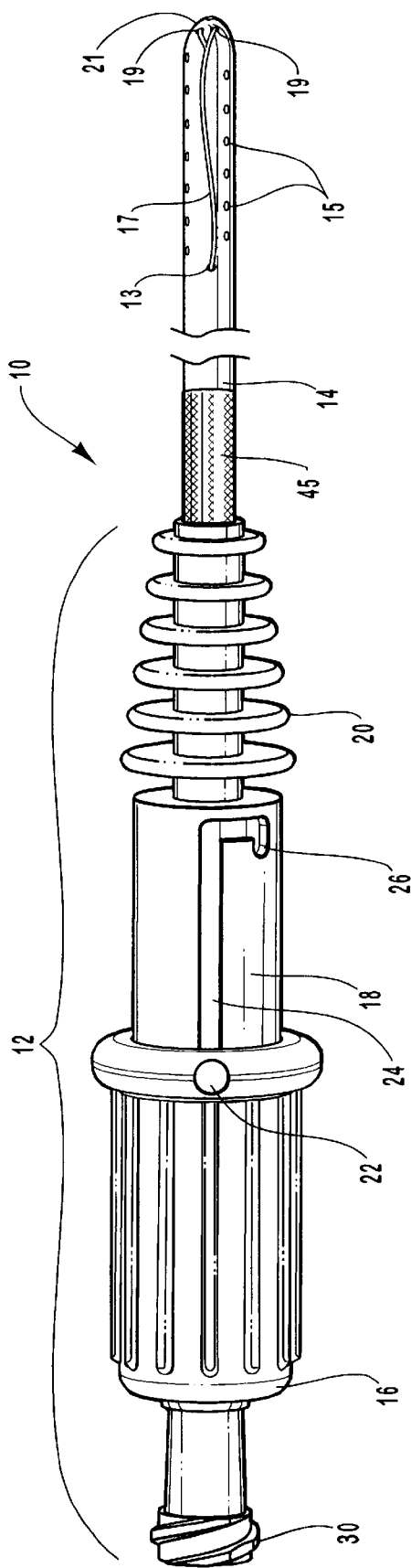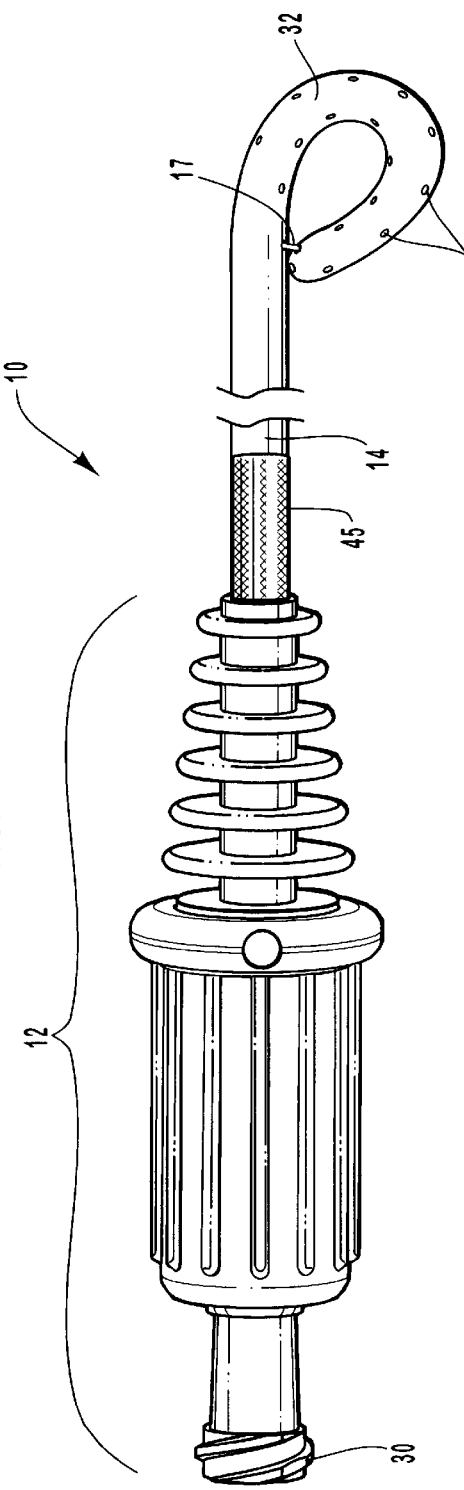

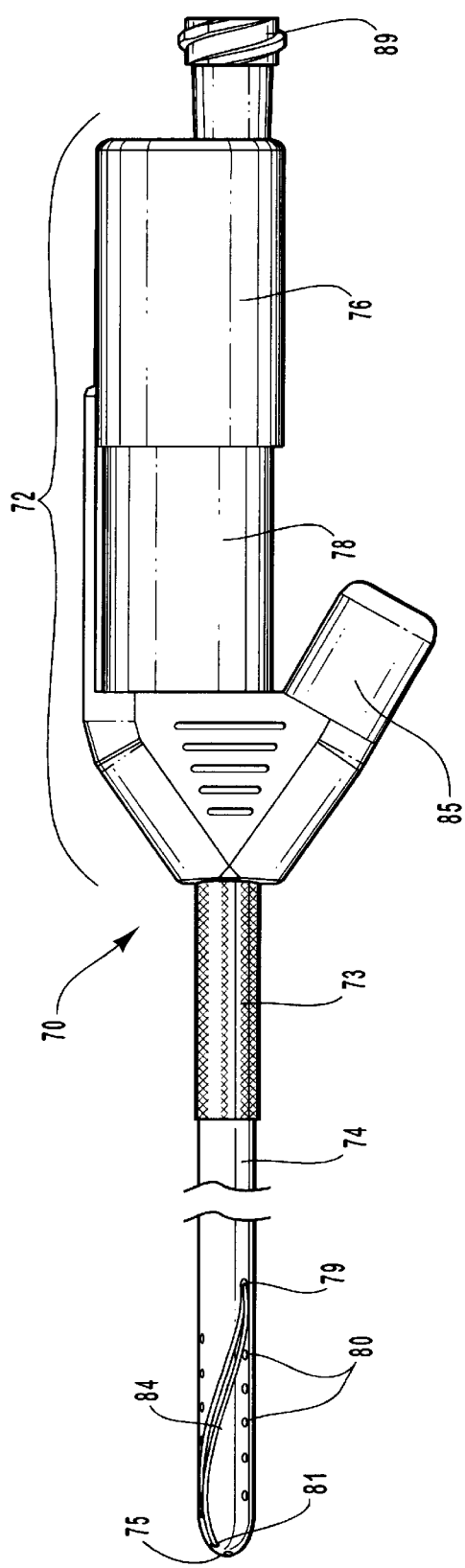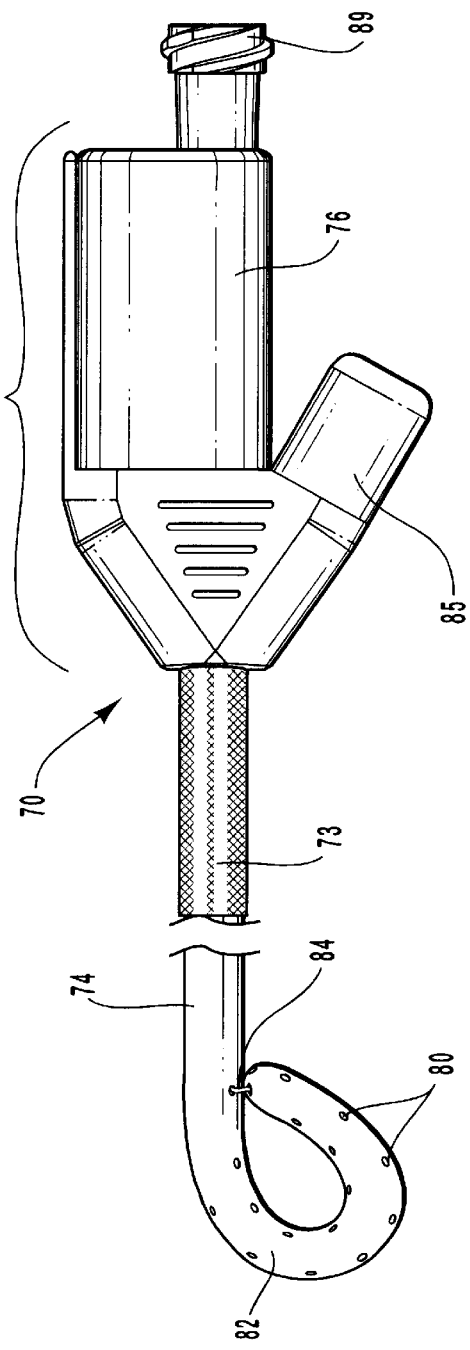
FIG. 7
FIG. 8

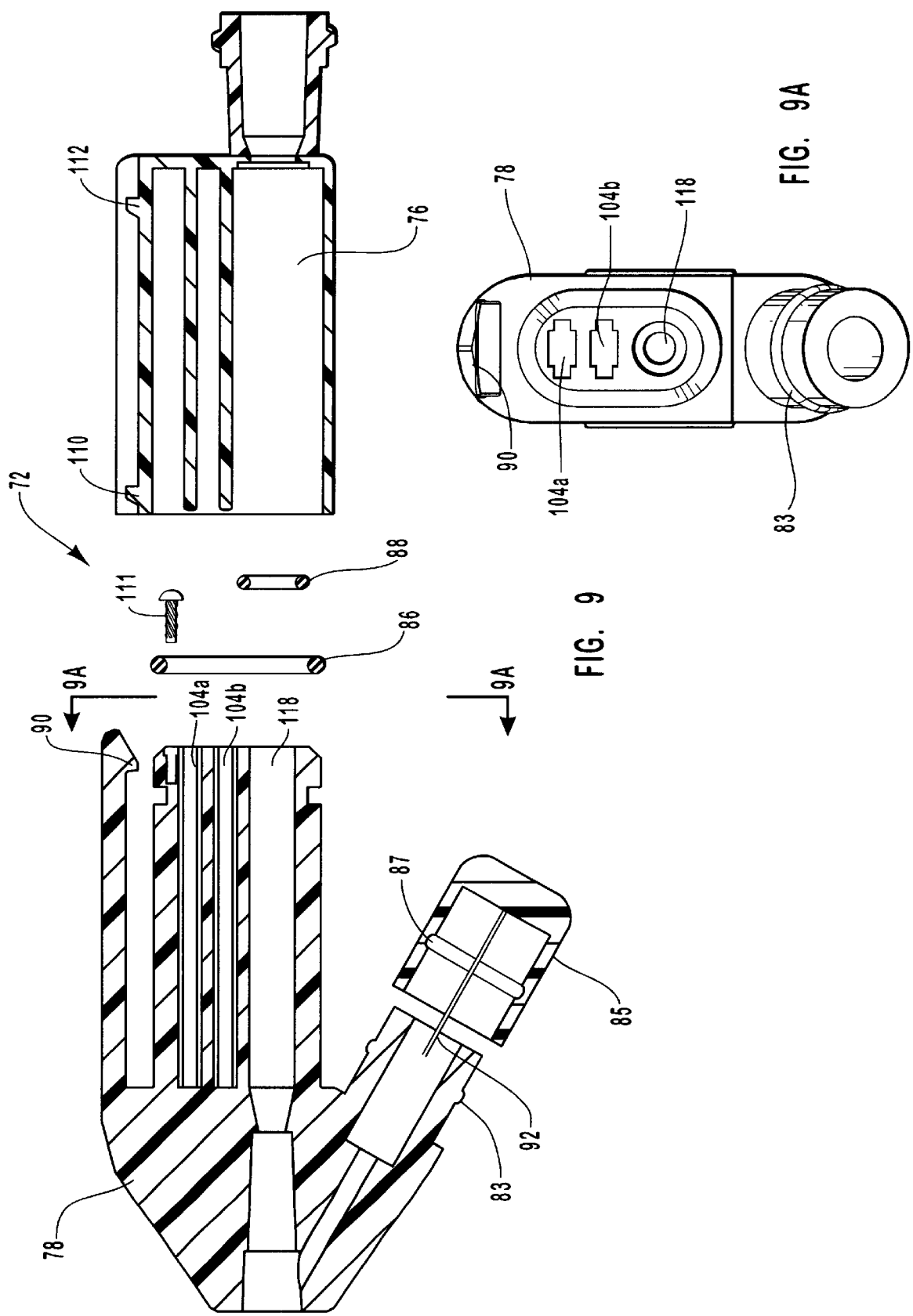

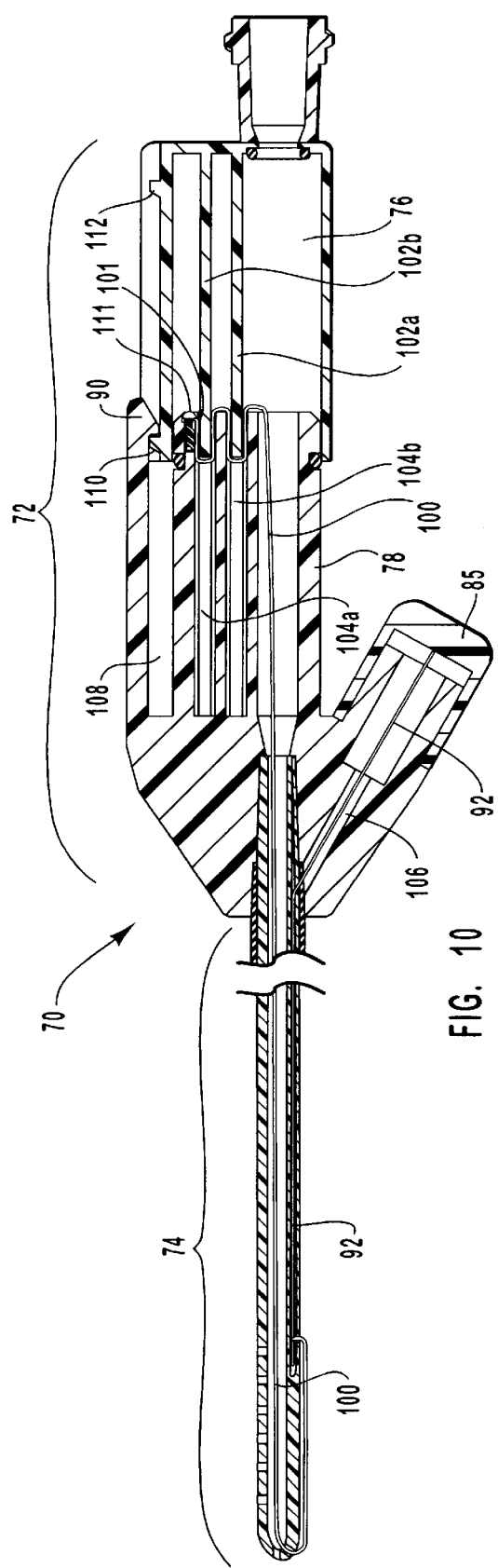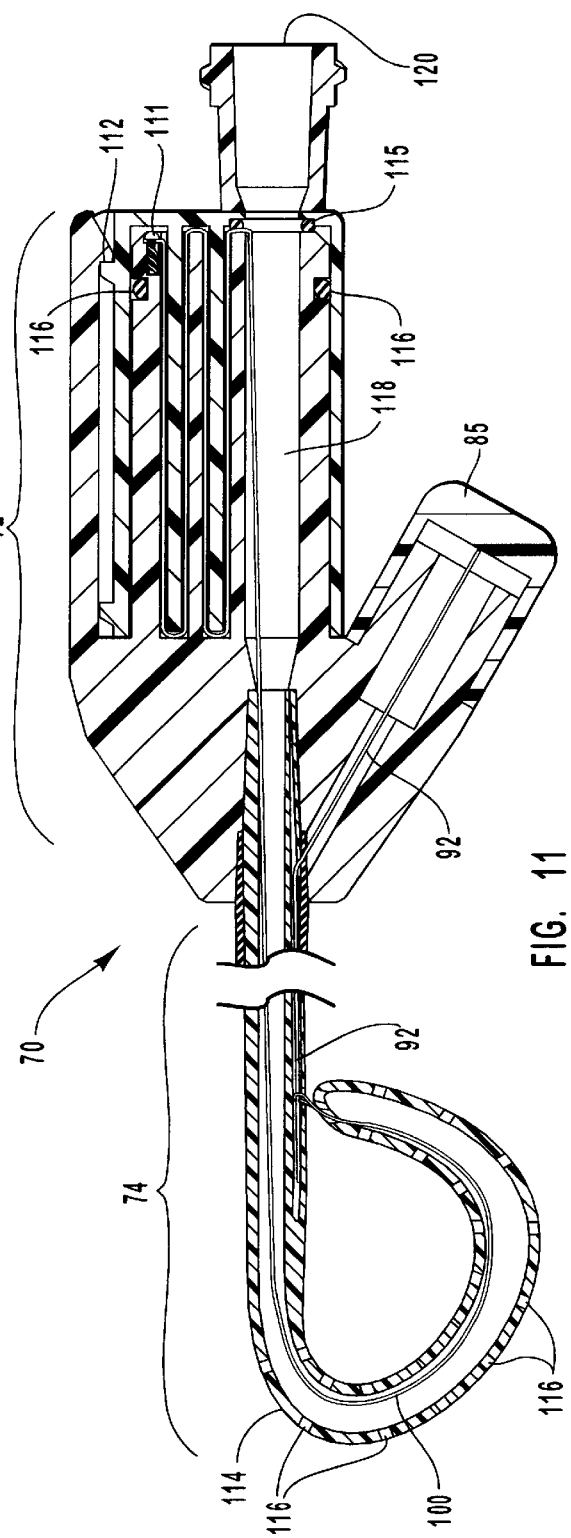

SYSTEMS AND METHODS FOR COUPLING A DRAINAGE CATHETER TO A PATIENT AND DECOUPLING THE DRAINAGE CATHETER FROM THE PATIENT

BACKGROUND OF THE INVENTION

1. The Field of the Invention

The present invention relates to catheter systems and more particularly to drainage catheter systems that are used for draining bodily fluids from a patient. The present invention is also directed to methods for coupling a drainage catheter system to a patient's body and decoupling the drainage catheter from the body.

2. The Prior State of the Art

One of the traditional methods for draining bodily fluids includes inserting a catheter into a cavity of a patient's body. The catheter is typically introduced either over a previously inserted guide wire or by direct puncture. Catheters are used in procedures for draining bodily fluids from, by way of example, the kidneys, the liver, and from other organs. Catheters are also used to drain bodily fluid from the chest, abdominal cavities, and from abscesses located in various areas of the body. One of the challenges of using a catheter for draining bodily fluid is its propensity to be accidentally removed from a patient's body. Catheters have traditionally included straight tubing that, upon movement of the patient or accidental collision, can escape the patient's body. In order to prevent displacement of the tubing from the patient's body, various catheters have been developed that are configured to be anchored inside the patient's body.

FIGS. 1A–1C provide an example of the traditional method for forming a loop at the distal end of the tubing in order to prevent displacement of the tubing from a patient's body. In FIG. 1A, a traditional drainage catheter is illustrated generally as catheter 1, which includes hub 2 and tubing 3. As illustrated, one end (not shown) of a cord, such as cord 4, is affixed to the inside of hub 2, while the opposing end of cord 4 extends through tubing 3. Cord 4 extends from hub 2 inside tubing 3, then out of an exit opening at the distal end of the tubing such as opening 7. Cord 4 then extends back into a side entrance opening such as opening 6, through tubing 3 and out of the proximal end of hub 2, such that a free end of cord 4 is disposed outside hub 2, as shown in FIG. 1A.

Upon inserting catheter 1 into the patient's body, the free end of cord 4 that protrudes out of hub 2 can be pulled tight, causing a loop to be formed in tubing 3, as illustrated in FIG. 1B as loop 9. Loop 9 maintains catheter 1 within the selected portion of the body. The bodily fluid drains into the catheter via entrance openings such as openings 5 illustrated in FIGS. 1A–1C. Once the bodily fluid drains into the entrance openings, the fluid flows down tubing 3, and out of hub 2.

Cord 4 must maintain its tension in order for loop 9 to remain in the tubing. Therefore, traditional methods have included securing the free end of cord 4 after it has been pulled tight. As such, cord 4 is able to maintain its tension during the period that bodily fluid is drained from the patient. One of the methods for securing cord 4 after it has been pulled tight includes tying the free end of cord 4 to a fixed object, such as hub 2 of catheter 1, as illustrated in FIG. 1B at knot 8. However, while tying the free end of cord 4 to a fixed object maintains the tension in cord 4, problems arise with this traditional method.

One problem experienced by practitioners using this traditional method is that the process of tying the free end of cord 4 can become cumbersome. At times the challenge of securing cord 4 is so great that the free end cannot be tied. Moreover, when cord 4 is tied and secured, the knot can have tendencies to slip, thereby causing the tension in the cord to decrease. The decrease in cord tension causes the loop to relax.

Another problem with the traditional method includes a risk that is presented after the practitioner secures the free end of the cord. Once the cord is secured, the excess is cut off with a sharp instrument. The risk presented includes that the sharp instrument used to cut off the excess cord can cause an accidental laceration to the practitioner.

Another problem with the traditional method occurs during the extraction of the catheter from the patient's body. Under a traditional drainage catheter design, and as further illustrated in FIG. 1C, a cord, such as cord 4, extends through the tubing, exits through opening 7 located at the distal end of the tubing, and re-enters a side opening of the tubing at opening 6. Throughout the period of drainage into entrance openings, such as opening 5, cord 4 is exposed to bodily fluid, causing cord 4 to become encrusted. At the time when the tubing is to be removed from the patient's body, the encrustation of cord 4 can prevent tubing 3 from straightening out, thereby restricting the catheter from being easily removed from the patient. Therefore, the encrusted cord causes increased difficulty when extracting the catheter from the patient's body.

Another problem with the traditional method is presented when the catheter needs to be relocated, replaced, or removed. Once cord 4 is secured, it can be difficult to untie knot 8 of FIG. 1B. Therefore, the practitioner's ability to relocate, replace, or remove the catheter is restricted because of the difficulty to untie knot 8. Moreover, if the excess of cord 4 has been cut off, the cord may no longer be long enough to allow the catheter to be relocated.

It would, therefore, be an advancement in the art to be able to secure the catheter without having to tie the free end of a cord. It would also be desirable if the process of securing the catheter were simplified. Furthermore, it would be desirable if the process of securing the catheter could be performed by one hand. It would be an advancement in the art if the method of affixing the cord prevented any slippage that would cause the tension in the cord to relax. It would also be desirable if once secured, the excess cord did not have to be trimmed. Moreover, it would be an advancement in the art if the removal of the catheter from the patient's body was not affected by the encrustation of the cord.

SUMMARY OF THE INVENTION

The present invention is directed to drainage catheter systems, and to methods for coupling a drainage catheter system to a patient and decoupling the drainage catheter system from the patient. The invention overcomes the above-mentioned difficulties by facilitating the process of securing a catheter to the patient's body, and by facilitating the removal of the catheter from the body.

Implementation of the present invention takes place in association with a catheter, such as a drainage catheter used for draining bodily fluid from a patient. Embodiments according to the present invention include an elongate hollow cannula having a proximal end and a distal insertion end, a hub that can be placed in either an extended or contracted position, and a cord that extends from the hub and within at least a portion of the cannula. The cannula includes openings so that bodily fluid can enter. Once the bodily fluid enters the cannula, the fluid drains down the inside of the cannula and out of the hub.

The cord has first and second opposing ends and an intermediate portion therebetween. The cord extends within at least a portion of the cannula and can be attached to the distal insertion end of the cannula in a variety of manners. In one embodiment, one end of the cord is attached to the hub with the intermediate portion of the cord extending through the cannula, exiting a side opening in the cannula, entering a first opening in the distal insertion end of the cannula, exiting a second opening in the distal insertion end of the cannula, and extending down through the cannula, with the second end of the cord attached to the hub. Optionally, the cord can resemble a lasso, having a loop on a first end that is fastened to the distal insertion end of the cannula. The cord then enters the cannula through a side opening and the second end is attached to the hub.

In another embodiment, a wire extends longitudinally through at least a portion of the cannula and can be used to secure the cord. In this embodiment, a first end of the cord is attached to the hub and the intermediate portion of the cord extends down the cannula, out an opening at the distal end of the cannula, through a side opening in the cannula, loops around the wire, exits the cannula through the side opening, reenters the cannula through the opening at the distal end of the cannula, and extends along the length of the cannula to the hub, with the second end of the cord attached to the hub. Similarly, the cord can resemble a lasso, with a loop at a first end. A wire extends through the loop to secure the cord. The cord extends out of a side opening of the cannula, re-enters the cannula through a distal opening, and extends down the cannula, with the second end of the cord attached to the hub.

The catheter cannula can be inserted into a patient's body by way of a previously inserted guide wire, or by direct puncture, for example. Once inside of the patient's body, the catheter can be coupled to the body by pressing a proximal hub member towards a distal hub member to place the hub into a compressed position. In one embodiment, by pressing the proximal hub member towards the distal hub member, one or more fingers within the proximal hub member pushes the cord into channels within the distal hub member, causing the cord to create a force upon the distal insertion end of the cannula, in the direction of the hub. The force causes the distal insertion end of the cannula to form a loop that prevents the removal of the catheter from the patient's body. In one embodiment, the proximal and distal hub members can be locked together in the contracted position for as long as the catheter is to be coupled to the body.

To permit extraction of the catheter, the tension is eliminated from the cord. In the embodiments employing a wire, the wire is moved in a proximal direction in the cannula, thereby releasing the cord from the wire, eliminating the tension in the cord, and enabling the removal of the catheter cannula from the body. In another embodiment, a tear through material is employed in the cannula. In this embodiment, the cord can be pulled to cause the cord to tear through the distal insertion end of the cannula, thereby eliminating the tension in the cord and enabling the removal of the cannula from the patient's body. In yet another embodiment, the proximal and distal hub members are unlocked and slid apart to eliminate the tension in the cord and to enable uncurling of the catheter distal insertion end and the removal of the cannula from the patient's body.

Additional features and advantages of the present invention will be set forth in the description that follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order that the manner in which the above recited and other advantages and features of the invention are obtained, a more particular description of the present invention briefly described above will be rendered by reference to specific embodiments thereof that are illustrated in the appended drawings. Understanding that the drawings depict only typical embodiments of the invention and are not therefore to be considered to be limiting of its scope, the invention will be described and explained with additional specificity and detail through the use of the accompanying drawings in which:

FIG. 1A illustrates an example of a traditional drainage catheter with a free end of a cord protruding out of the proximal end of the catheter hub;

FIG. 1B illustrates an example of the traditional drainage catheter of FIG. 1A with the cord pulled tight and tied around the hub to create and maintain a loop at the end of the catheter tubing;

FIG. 2 illustrates an exemplary embodiment of the present invention with the hub in an extended position;

FIG. 3 illustrates the exemplary embodiment of FIG. 2 with the hub in a contracted position;

FIG. 7 illustrates another exemplary embodiment of the present invention and includes a hub in an extended position;

FIG. 8 illustrates the exemplary embodiment of FIG. 7 with the hub in a contracted position;

FIG. 9 illustrates an exploded view of the exemplary embodiment of FIG. 7;

FIG. 9A illustrates a rear end view of the distal hub member of FIG. 9;

FIG. 10 illustrates a cross-sectional view of the exemplary embodiment of FIG. 7 with the hub in an extended position;

FIG. 11 illustrates a cross-sectional view of the exemplary embodiment of FIG. 7 with the hub in a contracted position;

DETAILED DESCRIPTION OF THE PREFERRED EMBODIMENTS

Figure 1C:
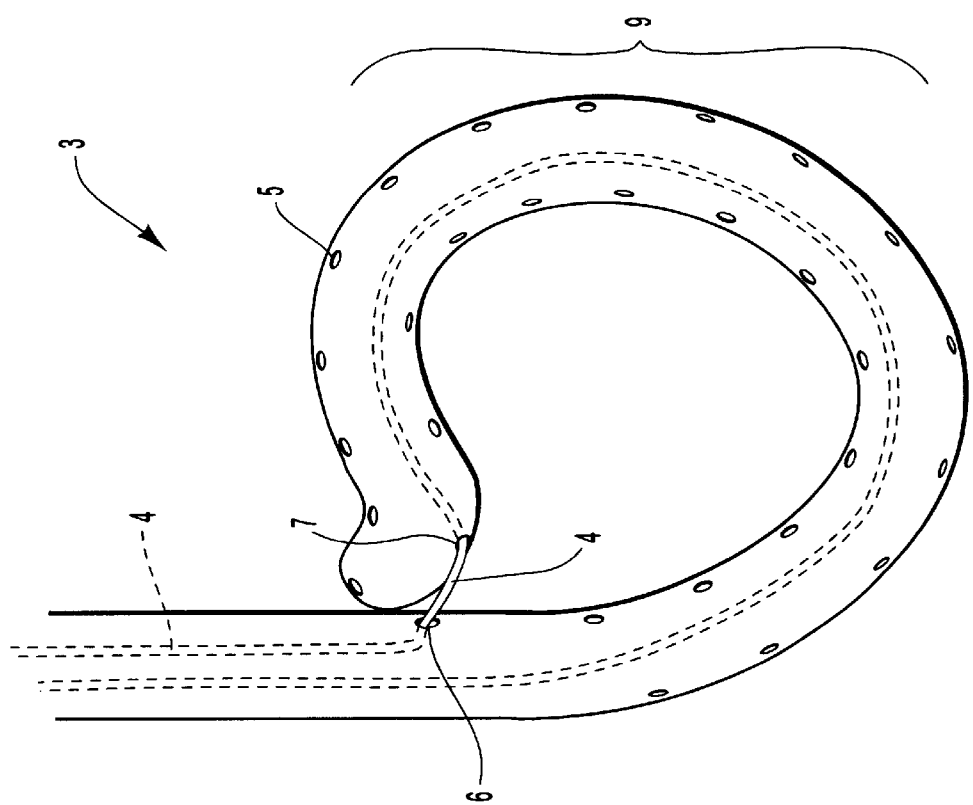
FIG. 1C illustrates a traditional method for threading a cord through the lumen of a catheter.

The description of the present invention utilizes diagrams that illustrate either the structure or processing of embodiments for implementing the systems and methods of the present invention. Using the diagrams in this manner to present the invention should not be construed as limiting its scope. Furthermore, the headings and subheadings employed in this description are for convenience of the reader only and are not to be construed as limiting in any sense.

The present invention relates to catheter systems and more particularly to drainage catheter systems that are used for draining bodily fluids. The present invention is also directed to methods for coupling a drainage catheter to a patient's body and decoupling the drainage catheter from the body, as will be further explained below. Those skilled in the art will appreciate that the invention may be practiced in combination with a variety of differently sized catheters.

The Hub and its Relationship to the Distal Insertion End of the Cannula

One manner in which the present invention facilitates the coupling of a catheter to a patient's body and eases the decoupling of the catheter from the body regards the design and workings of the hub, and its relationship to the distal insertion end of the cannula. A drainage catheter of the present invention includes a hub and a cannula that are in fluid communication with each other. FIGS. 2 and 3 provide an exemplary embodiment of the present invention, illustrated generally as catheter 10, which includes hub 12 and cannula 14.

Referring first to FIG. 2, hub 12 is comprised of a proximal member, such as proximal hub member 16, a distal member, such as distal hub member 18, a fluid pathway extending therethrough, and a locking mechanism. Proximal hub member 16 and distal hub member 18 are adjustably coupled together. By way of example, in one embodiment of the present invention, proximal hub member 16 can be pressed towards distal hub member 18, thereby placing hub 12 into a contracted position, as illustrated in FIG. 3. Similarly, proximal hub member 16 can be pulled away from distal hub member 18, thereby placing hub 12 into an extended position, as illustrated in FIG. 2. The illustrated embodiment further includes handle 20 for gripping onto distal hub member 18 to facilitate the process of placing hub 12 into a contracted or extended position.

A locking mechanism is an example of a locking means for selectively locking hub 12 in the contracted position. The locking mechanism can include a pin, a latch, a lever, or any other device or combination of devices that can hold proximal hub member 16 and distal hub member 18 in a specific position relative to each other.

By way of example, in the embodiment shown, the locking mechanism can include (i) a protrusion, such as pin 22, in proximal hub member 16; and (ii) a mating channel, such as channel 24 in distal hub member 18. When proximal hub member 16 is pushed toward distal hub member 18, pin 22 slides along channel 24. When in the fully contracted position, proximal hub member 16 can be rotated in such a way as to place pin 22 into locking portion 26 of channel 24. As such, hub 12 can be maintained in the contracted position illustrated in FIG. 3 without further effort by a practitioner. Pin 22 and channel 24 provide an example of a means for selectively locking hub 12 into a contracted position. In another embodiment, a second locking portion of the channel can maintain hub 12 in an extended position to facilitate the insertion of catheter 10 into a patient's body.

Referring back to FIG. 2, catheter 10 includes an elongate hollow cannula, such as cannula 14. Cannula 14 is a flexible, elongate tube having a proximal end in fluid communication with hub 12, a distal insertion end for insertion into a cavity of the body and a plurality of openings. By way of example, openings 15 allow for bodily fluid to enter cannula 14; opening 13 allows cord 17, which is attached to hub 12 and extends within at least a portion of cannula 14, to exit cannula 14; and openings 19 allow for the attachment of cord 17 to distal insertion end 21 of cannula 14, as will be further explained below. The insertion of cannula 14 into a body is performed while hub 12 is in an extended position.

As illustrated in FIG. 3, once cannula 14 is inserted in the desired cavity of the patient's body, cannula 14 is manipulated to form an anchoring configuration, such as loop 32, inside of the body to couple catheter 10 to the body and prevent cannula 14 from being inadvertently removed. The use of the cord in a variety of manners allows for the formation of a number of different kinds of configurations that can be formed to couple the catheter to the patient's body. By way of example, the anchoring configuration may include a pigtail, a j-curve, a malecot having one or more wings, and so forth, as will be further explained below.

Placing hub 12 into a contracted position causes an anchoring configuration to form, such as loop 32, by placing tension on cord 17 and causing distal insertion end 21 of cannula 14 to approach opening 13, as will be further explained below. Cannula 14 remains in the patient's body as long as catheter 10 is used for draining bodily fluid. While cannula 14 is in the body, bodily fluid can enter catheter 10 through openings 15, drain through cannula 14, into hub 12, and out of the end of hollow connector 30 of FIG. 3.

Once the bodily fluid is removed from the cavity, catheter 10 is decoupled from the body. The decoupling takes place by first twisting proximal hub member 16 to cause pin 22 to leave locking portion 26 of channel 24. Proximal hub member 16 can then be pulled away from distal hub member 18 to cause pin 22 to slide proximally along channel 24, and place hub 12 back into an extended position. After hub 12 is moved from a contracted position to an extended position, the anchoring configuration, such as loop 32, can be straightened to allow cannula 14 to be removed from the body.

In another embodiment, catheter 10 is decoupled from the body by pulling on cord 17, causing distal insertion end 21 of cannula 14 to tear and detach cord 17 from distal insertion end 21. In one embodiment, the proximal hub member 16 is removed from the distal hub member 18 to allow access to cord 17. Once cord 17 is accessible, cord 17 can be pulled to cause distal insertion end 21 of cannula 14 to tear and detach cord 17 from distal insertion end 21. In another embodiment, the attachment of cord 17 to hub 12 further includes the attachment of cord 17 to proximal hub member 16 so that when the proximal hub member 16 is pulled away from the distal hub member 18, cord 17 is also pulled to cause distal insertion end 21 of cannula 14 to tear and detach cord 17 from distal insertion end 21.

Figure 4:
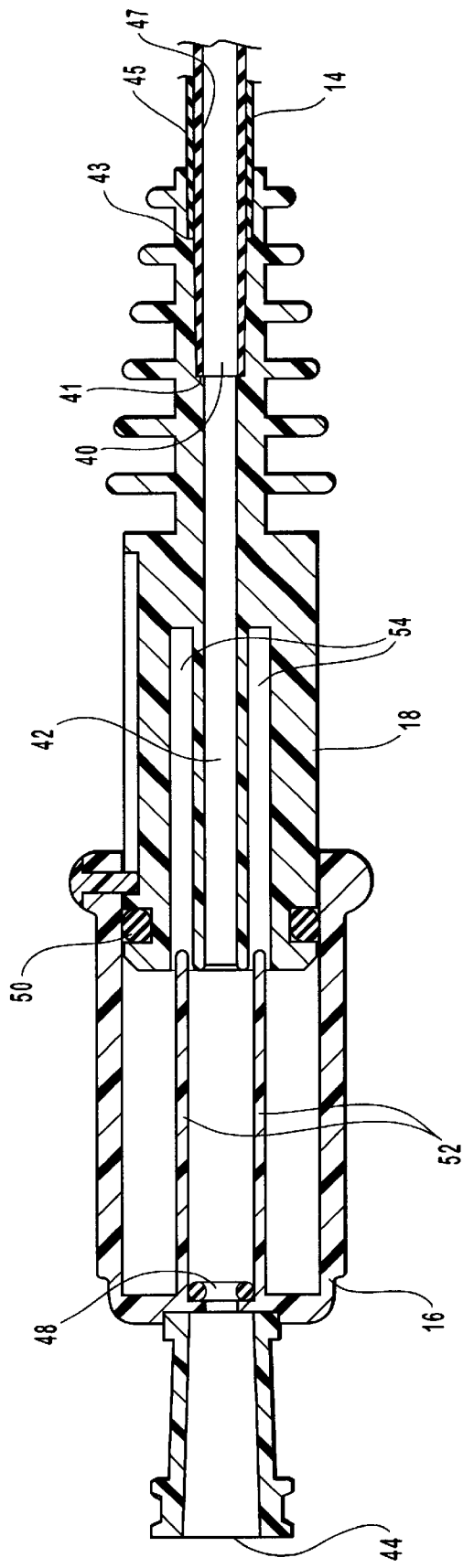
FIG. 4 illustrates a cross-sectional view of the exemplary embodiment of FIG. 2 with the hub in an extended position without the cord in place.

Referring now to FIG. 4, a cross-sectional diagram of hub 12 is provided to illustrate an embodiment of the present invention. For illustration purposes, a cord is not included. As illustrated in FIG. 4, in one embodiment cannula 14 is coupled to hub 12 by being inserted into a cavity of distal hub member 18, such as cavity 40, and abuts annular ridge 41, thereby enabling hub 12 and cannula 14 to be in fluid communication with each other. Strain relief tube 45 abuts annular ridge 43 and surrounds a portion 47 of cannula 14 to provide additional support. Hub 12 and cannula 14 are hollow, thereby allowing bodily fluid to run from cannula 14, through hub 12 via a fluid pathway extending therethrough, such as canal 42, and out of proximal end 44 of catheter 10. Two gaskets, such as rubber O-rings 48 and 50, are positioned at an interface between proximal hub member 16 and distal hub member 18 to prevent the bodily fluid from flowing into undesirable locations.

In one embodiment of the present invention, and as illustrated in FIG. 4, proximal hub member 16 includes cylinder 52 and distal hub member 18 includes channel 54, such that when proximal hub member 16 is selectively and removably pushed toward distal hub member 18, cylinder 52 extends into channel 54 of distal hub member 18. As will be explained in relation to FIGS. 5 and 6 below, when a cord is attached to the hub, cylinder 52 functions as a finger that pushes the cord into channel 54 as proximal hub member 16 is pushed toward distal hub member 18, thereby causing cannula 14 to form an anchoring configuration (i.e. a loop, j-curve, pigtail, malecot, etc.) when hub 12 is in a contracted position. In another embodiment, one or more fingers can be included that slide into one or more corresponding channels, thereby pushing a cord into the channels.

Figure 5:
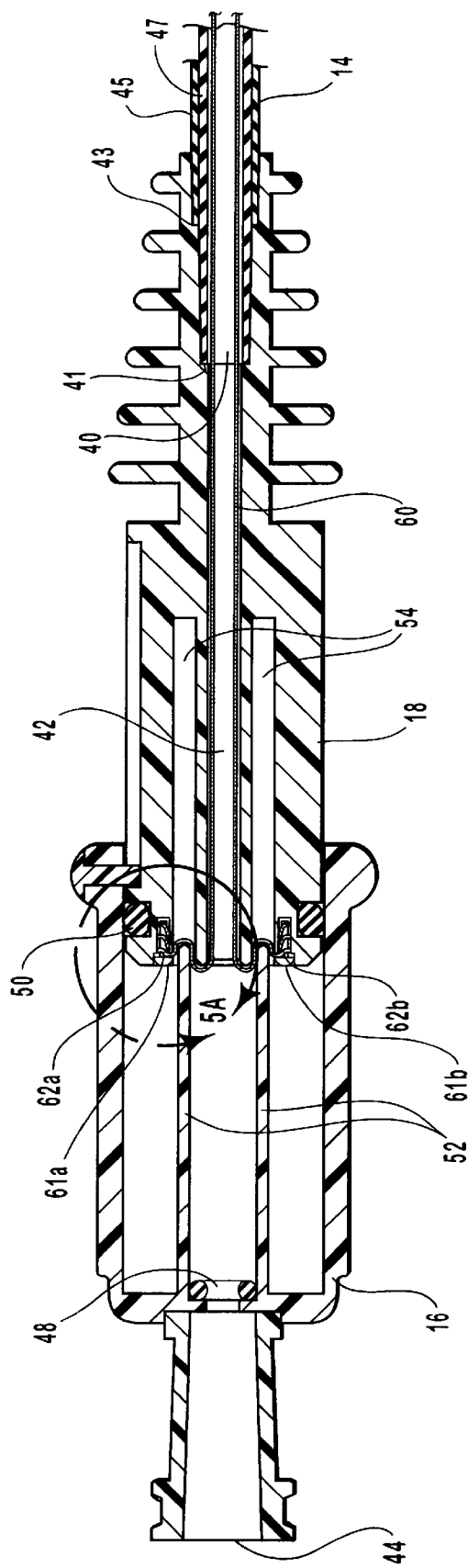
FIG. 5 illustrates a cross-sectional view of the exemplary embodiment of FIG. 2 with the hub in an extended position, and with a cord threaded through the hub such that both ends of the cord are affixed to the distal hub member.

Referring to FIG. 5, a cross-sectional illustration of hub 12 in an extended position is provided that includes a cord, illustrated as cord 60. The cord can be made from a variety of materials, such as, by way of example, silk, nylon, polyethylene, suture material, or a variety of other materials to allow cord 60 to be sufficiently flexible that it can be selectively pushed into or removed from one or more channels inside of the hub, yet is strong enough to handle the required tension.

In the embodiment illustrated in FIG. 5, both of the opposing ends of cord 60 are affixed to hub 12. More specifically, both ends 62a and 62b of cord 60 are affixed to the proximal end of distal hub member 18. (An exemplary manner of affixing ends 62a and 62b will be discussed below in association with FIG. 5A.) The intermediate portion of cord 60 extends through canal 42 within cannula 14. Therefore, in the embodiment illustrated in FIG. 5, when proximal hub member 16 is pushed toward distal hub member 18, cylinder 52 forces cord 60 to enter into channel 54, thereby increasing the amount of cord 60 within hub 12 and reducing the amount of cord 60 within cannula 14. Since the intermediate portion of cord 60 is selectively attached to the distal insertion end of cannula 14, the reduction of the amount of cord 60 in cannula 14 causes an anchoring configuration (i.e. a loop, j-curve, pigtail, malecot, etc.) to form at the distal insertion end of cannula 14, as shown in FIG. 3.

Figure 5A:
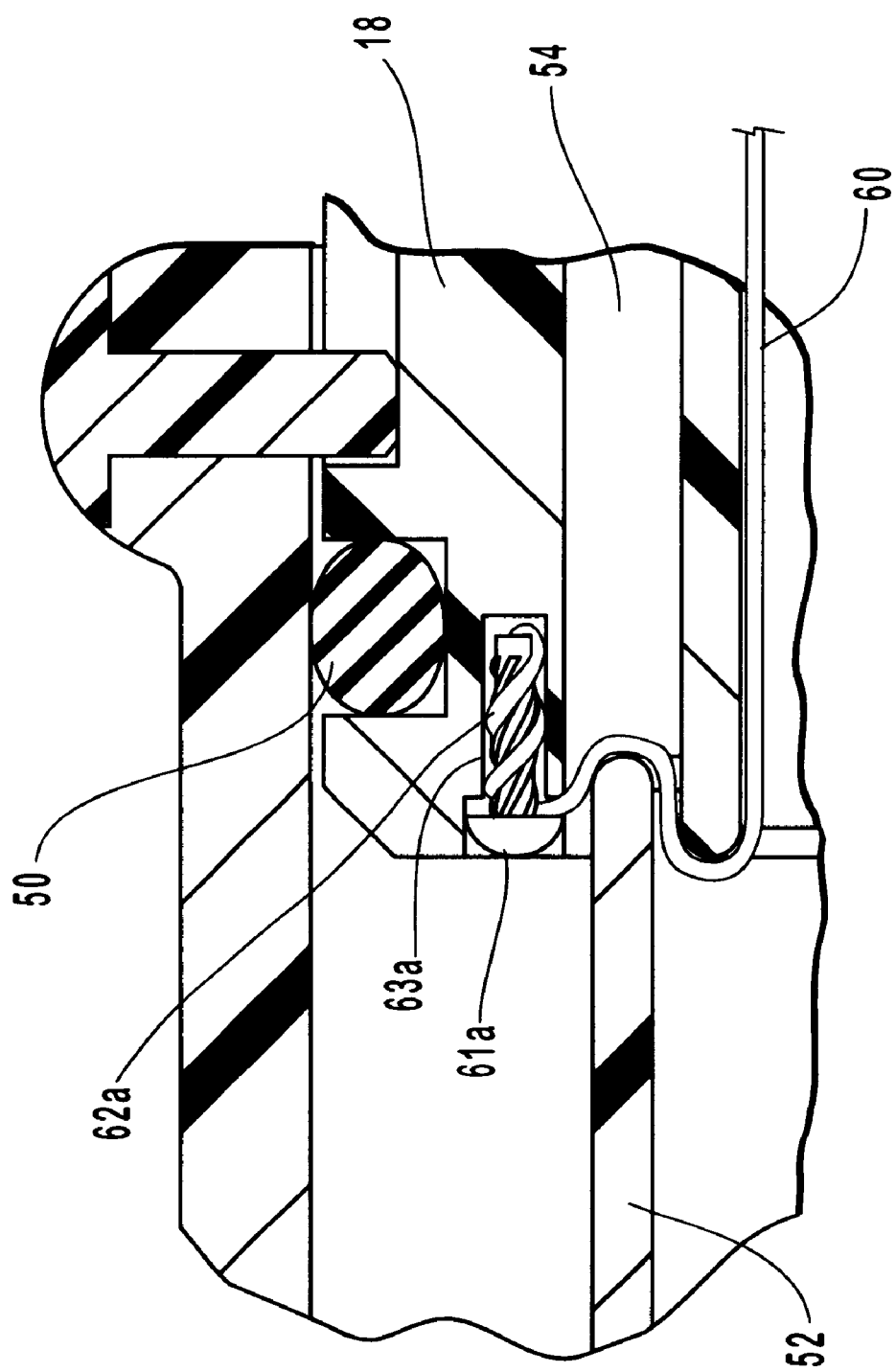
FIG. 5A illustrates an exemplary manner of affixing an end of a cord to a hub.

FIG. 5A illustrates an exemplary manner of affixing the opposite ends of cord 60 to hub 12. In FIG. 5A, a first end of cord 60, such as, by way of example, end 62a, is wrapped around pin 61a. To secure end 62a to hub 12, pin 61a is inserted (i.e., by being threaded or pushed) into aperture 63a of, by way of example, the proximal end of distal hub member 18. An adhesive can be used to ensure that pin 61a is maintained in aperture 63a. Other manners of affixing the opposite ends of cord 60 to hub 12 include the use of insert molding, an adhesive, a snap ring, a C-clamp, or the like, as will be further discussed below.

Figure 6:
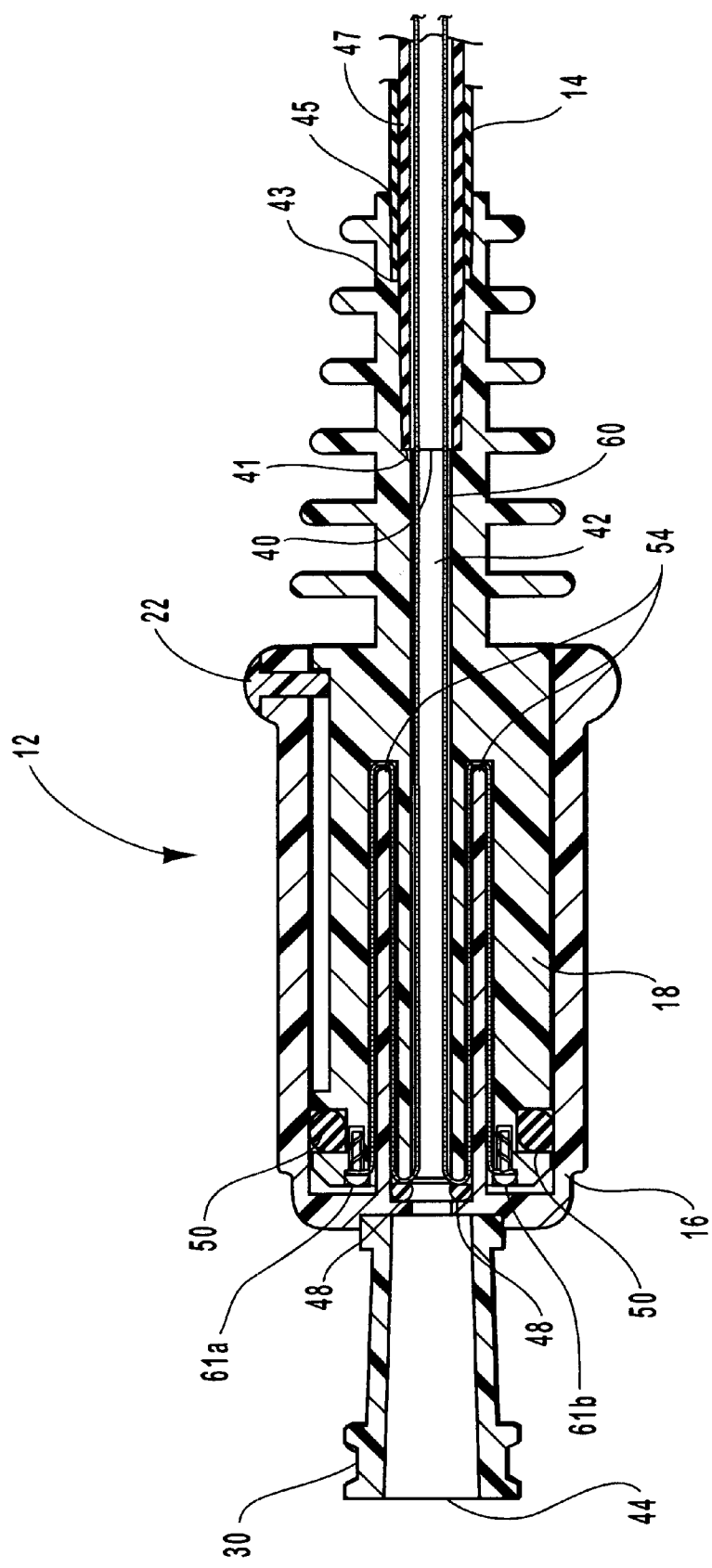
FIG. 6 illustrates a cross-sectional view of the exemplary embodiment of FIG. 2 with the hub in a contracted position demonstrating how the finger of the proximal hub presses the cord into a channel of the distal hub member causing tension on the cord.

FIG. 6 illustrates hub 12 in a contracted position with cord 60 pressed into channel 54. In this position an anchoring configuration (i.e. a loop, j-curve, pigtail, malecot, etc.), such as loop 32 of FIG. 3, is formed in distal insertion end of cannula 14. Once compressed, hub 12 can be maintained in a contracted position by employing a locking mechanism. In FIG. 6, pin 22 has been placed in locking portion 26 of channel 24 of FIG. 2 to maintain hub 12 in the contracted position.

As explained above, hub 12 includes O-rings 48 and 50 positioned at an interface between proximal hub member 16 and distal hub member 18 to prevent bodily fluid from flowing into undesirable locations. As illustrated in FIGS. 5 and 6, O-ring 48 prevents bodily fluid from entering channel 54 when hub 12 is in a contracted position. As such, the bodily fluid that flows through canal 42 is directed out proximal end 44. O-ring 50 prevents any bodily fluid from escaping between proximal hub member 16 and distal hub member 18. Therefore, when hub 12 is in an extended position as illustrated in FIG. 5, if any fluid happens to enter channel 54, when proximal hub member 16 and distal hub member 18 are pushed together the fluid is forced into canal 42 and drains out proximal end 44.

The opposing ends of cord 60, illustrated as ends 62a and 62b, can be affixed to distal hub member 18 through a variety of different coupling means. By way of example, the coupling means can include an insert molding, an adhesive, a pin (as illustrated in FIG. 5A), a snap ring, a C-clamp, or the like. Connector 30 may be coupled to a fluid collector, for example, which collects the bodily fluid that drains out of the catheter.

Referring now to FIGS. 7 and 8, another exemplary embodiment of the present invention is provided. The embodiment is illustrated generally as catheter 70, which includes hub 72 and cannula 74. In a similar manner as explained above, hub 72 is comprised of a proximal member, such as proximal hub member 76, a distal member, such as distal hub member 78. A fluid pathway extends through proximal and distal hub members 76, 78. Proximal hub member 76 and distal hub member 78 are adjustably coupled together in such a way as to selectively allow proximal hub member 76 to approach distal hub member 78, thereby placing hub 72 into a contracted position.

The contracted position of hub 72 is illustrated in FIG. 8. When in the contracted position, a locking mechanism, as will be further explained below, can be used to selectively and removably lock hub 72 in the contracted position. Thus, proximal hub member 76 can also be selectively allowed to retract from distal hub member 78, thereby placing hub 72 into an extended position, as illustrated in FIG. 7. In a further embodiment, the locking mechanism can also be used to selectively and removably lock hub 72 in an extended position. The locking mechanism may also allow for the complete decoupling of proximal hub member 76 from distal hub member 78. As provided above, the locking mechanism is an example of a locking means for selectively locking the proximal and distal hub members in the contracted position.

Referring back to FIG. 7, catheter 70 includes an elongate hollow cannula, such as cannula 74, that is in fluid communication with hub 72. Cannula 74 is a flexible, elongate tube that can be inserted into a cavity of the body for drainage of bodily fluid, and includes a variety of fluid entrance openings 80. A strain relief tube 73 can surround a portion of cannula 74 to provide additional support. Cannula 74 includes primary and secondary lumens, the primary lumen configured to receive fluid flowing therethrough and the secondary lumen configured to receive a wire therethrough, where the wire is any metallic or non-metallic elongate member, such as, by way of example, plastic, composite, etc., as will be further explained below. Cannula 74 is an example of cannula means for defining a primary lumen and a secondary lumen.

The insertion of cannula 74 into a body is performed while hub 72 is in an extended position. As illustrated in FIG. 8, once cannula 74 is inserted into the desired cavity of the body, hub 72 can be contracted such that cannula 74 forms an anchoring configuration inside the body, such as loop 82, thereby coupling catheter 70 to the patient's body and preventing cannula 74 from being inadvertently removed from the body.

Catheter 70 includes a cord illustrated as cord 84. A first end of cord 84 is attached to hub 72. Cord 84 then extends down cannula 74, exits distal insertion end 75 through opening 81, reenters cannula 74 at opening 79, wraps around a wire that extends longitudinally through at least a portion of cannula 74, exits cannula 74 at opening 79, enters distal insertion end 75 through opening 81, and extends down cannula 74, with the second end of cord 84 attached to hub 72. Placing hub 72 into a contracted position creates tension on cord 84, causing cord 84 to tighten, and causes an anchoring configuration to form at the distal end of cannula 74, thereby forming loop 82 and coupling catheter 70 to the patient's body. Cannula 74 remains in the body as long as catheter 70 is used for draining bodily fluid. The drainage takes place as the bodily fluid enters catheter 70 through openings 80, drains down cannula 74, through hub 72, and out of connector 89 at the proximal end of catheter 70.

Once the bodily fluid is removed from the cavity, catheter 70 can be decoupled from the body. In one embodiment, the decoupling takes place by removing cap 85, which has a wire attached that extends longitudinally through at least a portion of cannula 74. The removal of cap 85 and the corresponding wire allows for a simple removal of cannula 74 from the body, as will be further explained below.

Referring now to FIG. 9, an exploded, cross-sectional diagram of hub 72 is provided to illustrate an embodiment of the present invention. In the illustration, hub 72 includes proximal hub member 76, distal hub member 78, cap 85, a flexible wire 92, O-rings 86 and 88, a coupling means, such as pin 111, and a locking mechanism. Proximal hub member 76 and distal hub member 78 can be selectively slid together to place hub 72 into a contracted position or can be selectively slid away from each other to place hub 72 into an extended position. The locking mechanism is an example of a locking means for selectively locking the proximal and distal hub members in the contracted position, employing, by way of example, a protrusion and a channel. FIG. 9A provides an end view of distal hub member 78 into which proximal hub member 76 slides. Referring back to FIG. 9, O-rings 86 and 88 are positioned at an interface between proximal hub member 76 and distal hub member 78 to prevent bodily fluid from entering undesired locations, and a protrusion, such as hook 90, in connection with either protrusion 110 or protrusion 112 maintains hub 72 in either an extended position or a contracted position, all of which will be further explained below.

Distal hub member 78 includes primary and secondary lumens therein. The primary lumen is configured to receive fluid flowing therethrough and the secondary lumen is configured to receive at least a portion of a flexible wire therethrough. Affixed to cap 85 is wire 92 for assisting catheter 70 of FIG. 7 in being coupled to and decoupled from a patient's body. Cap 85 can fit onto distal hub member 78 in a variety of manners, such as, by way of example, a snap fit or by screwing onto distal hub member 78. In FIG. 9, a snap fit is illustrated that includes annular ridge 83 and mating annular groove 87. When cap 85 is fit onto distal hub member 78, annular ridge 83 fits into annular groove 87 to hold cap 85 on distal hub member 78. Cap 85 can be selectively fit onto or removed from distal hub member 78. Furthermore, since wire 92 is affixed to cap 85, the fitting of cap 85 onto distal hub member 78 inserts wire 92 into the secondary lumen of the cannula. Likewise, the removal of cap 85 from distal hub member 78 retracts wire 92 from the secondary lumen of the cannula.

FIGS. 10 and 11 illustrate cross sectional diagrams of catheter 70. In FIG. 10, catheter 70 is illustrated with hub 72 in an extended position. In FIG. 11, catheter 70 is illustrated with hub 72 in a contracted position. A locking mechanism can be used to selectively and removably lock hub 72 in the contracted position. The locking mechanism is an example of a locking means for selectively locking the proximal and distal hub members in the contracted position. The locking means utilizes, by way of example, a protrusion and a channel. Therefore, the locking mechanism illustrated in FIG. 11 includes, by way of example, hook 90 and protrusion 112, which when in contact with each other can maintain hub 72 in the contracted position.

The position of the proximal hub member 76 relative to the distal hub member 78 affects the distal insertion end of cannula 74. When hub 72 is in an extended position, the distal insertion end of cannula 74 can be extended so as to be in an extended position, as illustrated in FIG. 10. When hub 72 is in a contracted position, an anchoring configuration (i.e. a loop, j-curve, pigtail, malecot, etc.) is formed at the distal insertion end of cannula 74, as illustrated in FIG. 11.

As mentioned above, a cord can be used in a variety of manners to allow for the formation of a configuration to couple the catheter to the patient's body. By way of example, in FIGS. 7 and 8 a cord, labeled as cord 84, has a first end attached to the hub and the cord extends down the primary lumen of the cannula, exits the distal insertion end, reenters the cannula at a side opening, wraps around a wire that extends longitudinally through the secondary lumen of the cannula, exits the cannula, reenters the cannula at the distal insertion end, and extends down the primary lumen with the second end being attached to the hub. Alternatively, FIGS. 10 and 11 illustrate another manner of using a cord, opposed to the manner in which cord 84 of FIGS. 7 and 8 was used, to form a configuration such as a loop at the distal insertion end of the cannula. In FIGS. 10 and 11 the cord, labeled as cord 100, resembles a lasso, having a loop on a first end. The second end of cord 100, illustrated as end 101, is fastened to hub 72. By way of example, end 101 is fastened to hub 72 by an insert molding, an adhesive, a pin (as illustrated in FIG. 5A), a snap ring, a C-clamp, or the like. Cord 100 extends down the length of the primary lumen of cannula 74, exits an opening at the distal insertion end of cannula 74, and the looped end of cord 100 enters the secondary lumen of cannula 74 through a side opening. Wire 92 extends through the looped end of cord 100, as will be further explained below.

Tension on cord 100 can cause cannula 74 to form an anchoring configuration at the distal insertion end of cannula 74, such as loop 114 of FIG. 11. The tension is placed on cord 100 by pushing proximal hub member 76 toward distal hub member 78, thereby causing fingers 102a and 102b to push cord 100 into respective channels 104a and 104b. The pushing of cord 100 into channels 104a and 104b creates tension on cord 100 and results in the formation of loop 114.

The distal insertion end of catheter 70 is inserted into a cavity of a patient's body while hub 72 is in an extended position. Once inside the body, catheter 70 is coupled to the body by pushing proximal hub member 76 toward distal hub member 78, thereby causing loop 114 to form and preventing cannula 74 from accidentally escaping from the patient's body.

When proximal hub member 76 is pushed towards distal hub member 78, protrusions 110 and 112 slide into channel 108 of FIG. 10. Protrusion 112 and channel 108 act as a locking mechanism that locks hub 72 in a contracted position. As mentioned above, once hub 72 is in the fully contracted position, as illustrated in FIG. 11, hook 90 latches over protrusion 112, thereby causing hub 72 to be maintained in the contracted position. Protrusion 112 and channel 108 provide an example of a locking means for selectively locking the proximal and distal hub members in the contracted position.

Cannula 74 includes openings 116 whereby bodily fluid can enter. Once in the cannula, the bodily fluid flows down cannula 74, through channel 118, and out end 120. O-rings 115 and 116 are positioned at an interface between proximal hub member 76 and distal hub member 78 to prevent bodily fluid from entering into undesired locations. By way of example, O-ring 115 prevents the bodily fluid from entering channels 104a and 104b when hub 72 is in the contracted position. Similarly, O-ring 116 forces any bodily fluid out proximal end 120 that may have entered channels 104a and 104b while hub 72 was in an extended position. Therefore, O-rings 115 and 116 prevent bodily fluid from escaping from a portion of hub 72 other than proximal end 120.

As mentioned above, cap 85 can be fastened onto distal hub portion 78. Affixed to cap 85 is a flexible wire, such as wire 92. The flexible wire is any metallic or non-metallic elongate member, such as, by way of example, plastic, composite, etc. In the illustrated embodiment, wire 92 is made of nitinol. Wire 92 extends into hub 72 through lumen 106 of FIG. 10, down the secondary lumen of cannula 74, and is used for securing cord 100 to cannula 74 to enable the formation of an anchoring configuration in the distal insertion end of cannula 74 such as loop 114. The use of the flexible wire, such as wire 92, improves the structural integrity of cannula 74 by preventing kinking and allows for an easier insertion of cannula 74 into the patient's body by creating an amount of stiffness and strength to the catheter. Moreover, the stiffness and strength provided by the flexible wire allows for thinner walls of cannula 74 and a larger lumen size of the primary lumen of cannula 74 for a greater flow of bodily fluid. Upon removal or longitudinal displacement of cap 85 and wire 92, the looped end of cord 100 is released from wire 92. The releasing of the looped end of cord 100 from wire 92 releases the tension in cord 100, thereby allowing catheter 70 to be decoupled from the patient's body by removing cannula 74 from the body, as will be further explained below.

Figure 12A:
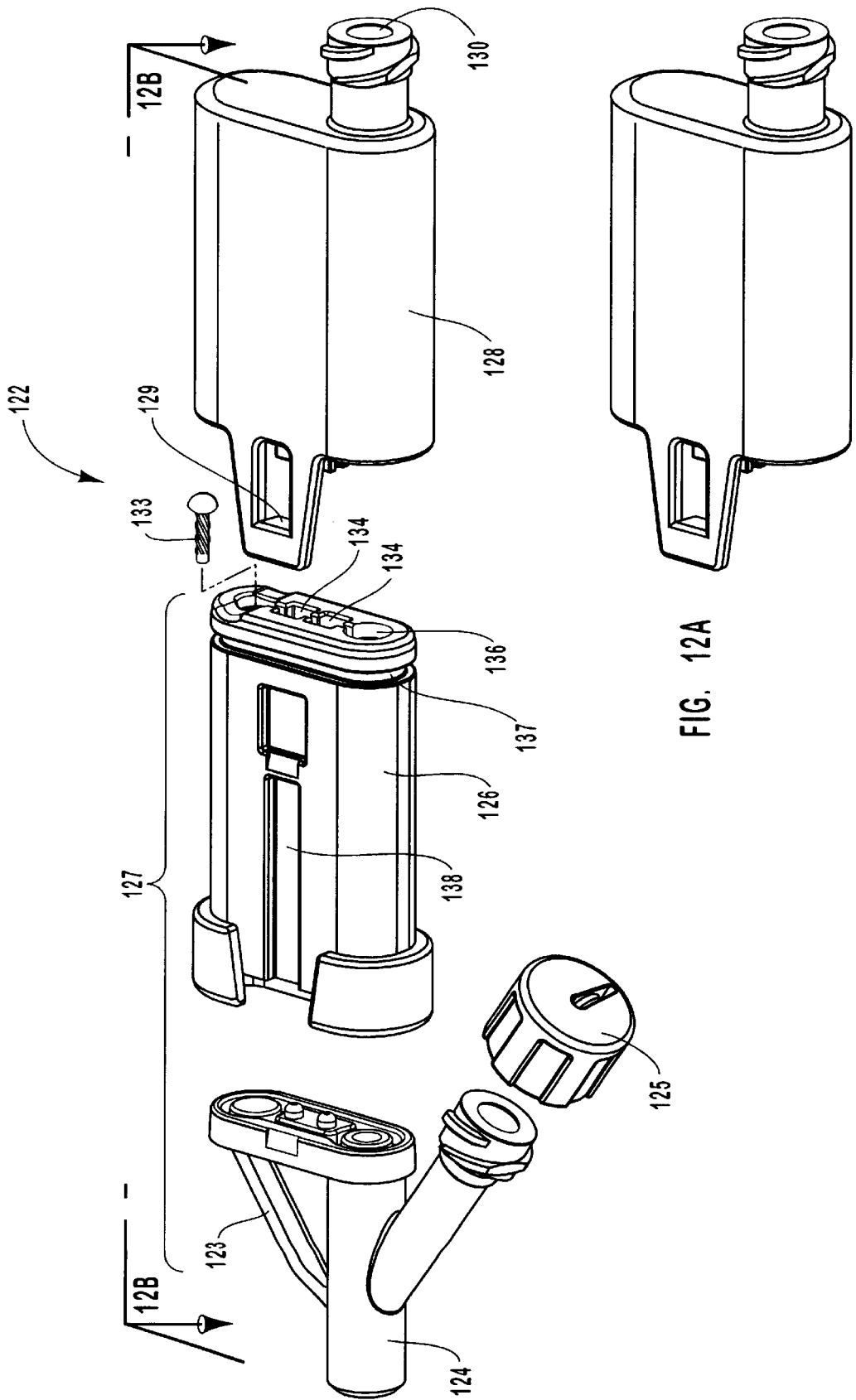
FIG. 12A illustrates an exploded view of another exemplary embodiment of the present invention.
Figure 12B:
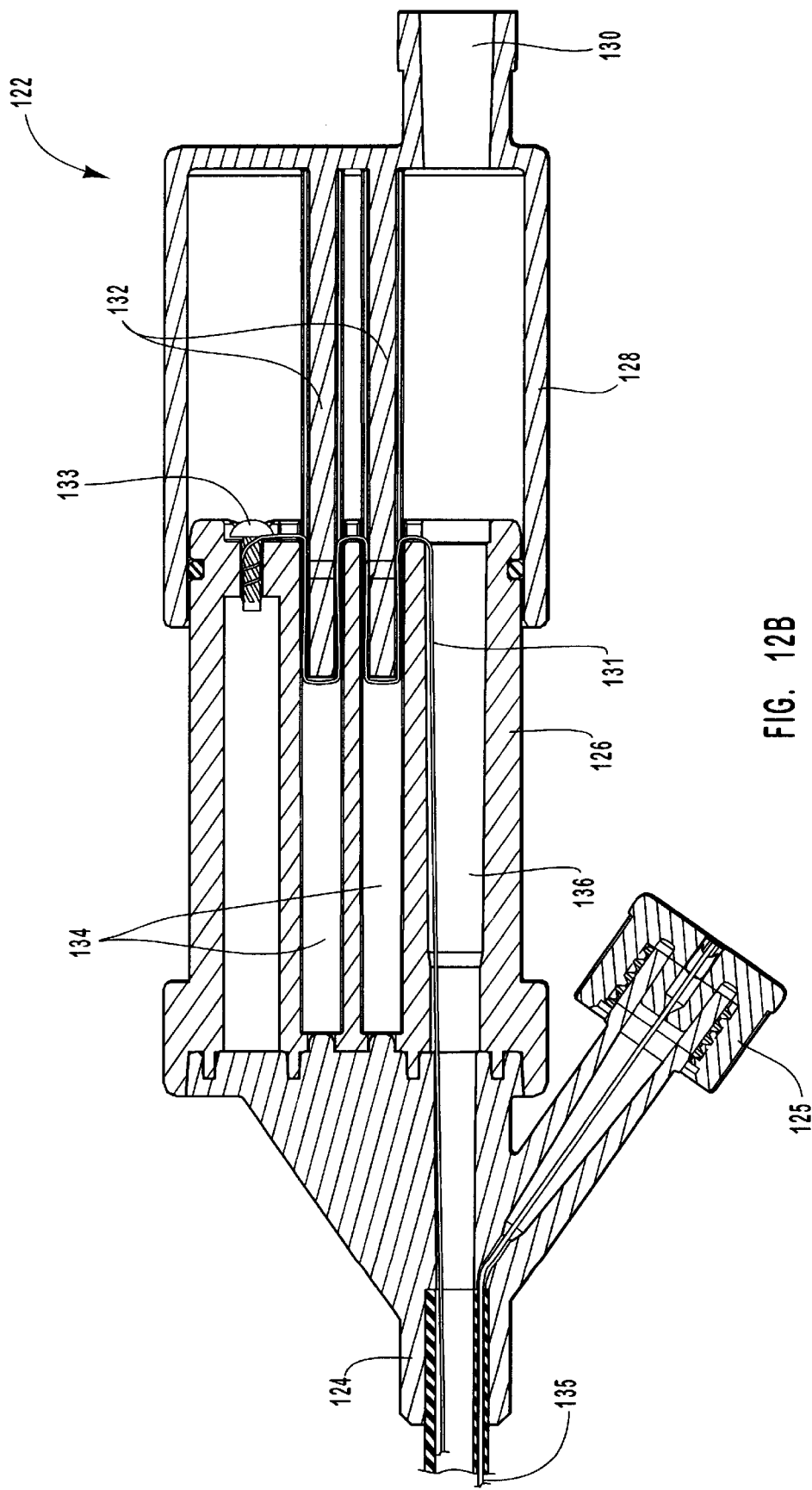
FIG. 12B illustrates the exemplary embodiment of FIG. 12A with the hub in an extended position.
Figure 12C:
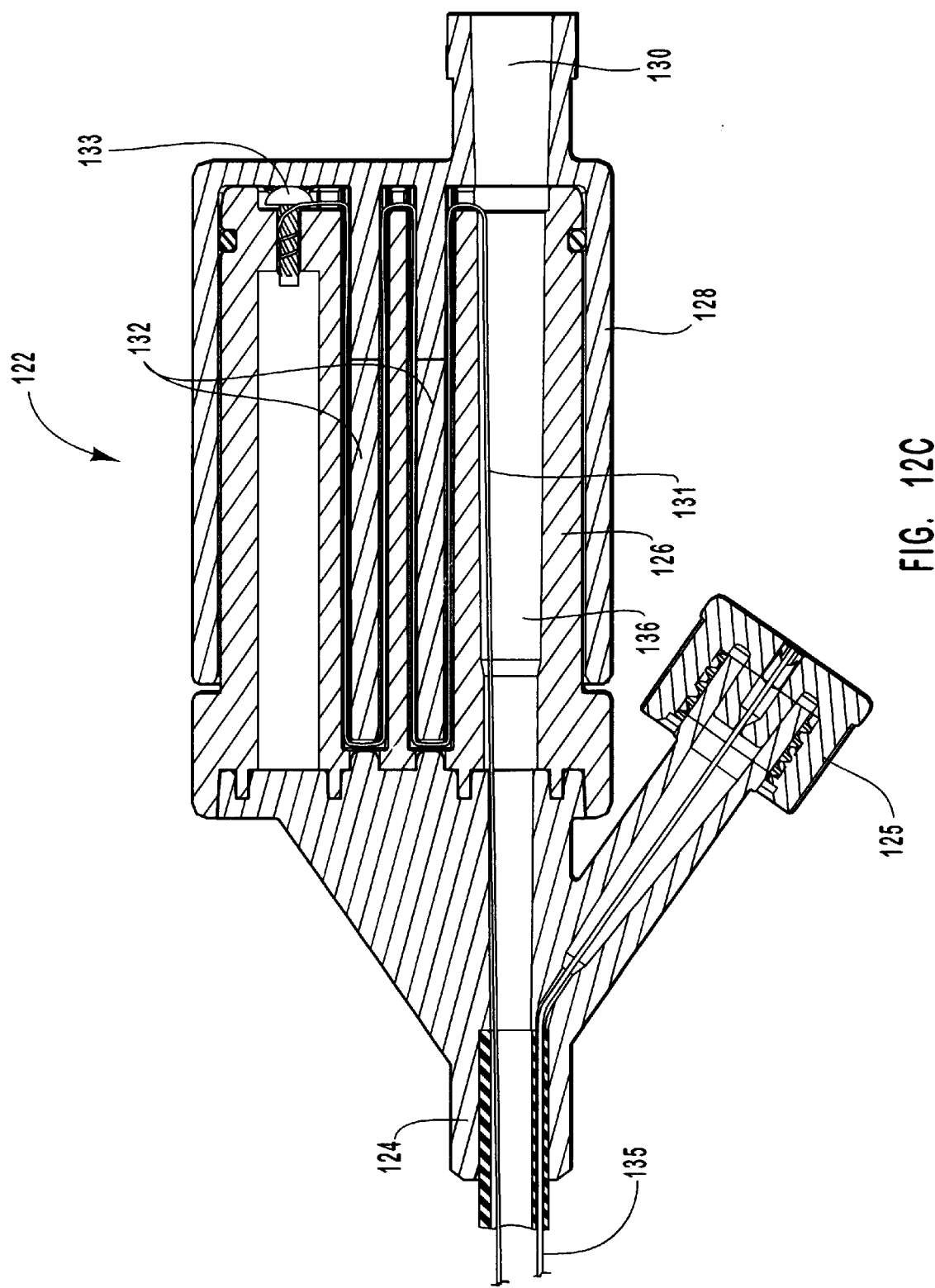
FIG. 12C illustrates the exemplary embodiment of FIG. 12A with the hub in a contracted position.

Another embodiment of the present invention is illustrated in FIGS. 12A–12C. FIG. 12A provides an exploded, cross-sectional diagram of hub 122. In FIG. 12A, hub 122 includes proximal hub member 128, and a two-part distal hub member 127. The two-part distal hub member comprises a first hub member 126 and a second hub member 124. First and second hub members can be combined to form distal hub member 127. In one embodiment, hub member 127 is initially formed in two parts which are conveniently combined in the molding and assembly process.

Hub 122 further includes support 123, cap 125, a coupling means, such as pin 133, and a locking mechanism, such as the combination of protrusion 129 and channel 138 which provide another example of a locking means for selectively locking the proximal and distal hub members in the contracted position. Proximal hub member 128 and distal hub member 127 can be selectively slid together to place hub 122 into a contracted position or can be selectively slid away from each other to place hub 122 into an extended position. Channel 137 provides a location for housing an O-ring. Also coupled to distal hub member 127 is an elongate cannula 135 (FIG. 12B) to form a drainage catheter.

Hub 122 includes primary and secondary lumens therein. The primary lumen is configured to receive fluid flowing therethrough and the secondary lumen is configured to receive at least a portion of a flexible wire therethrough. Affixed to cap 125 is the flexible wire (not shown) for assisting the drainage catheter in being coupled to and decoupled from a patient's body. For increased strength, one embodiment includes the proximal end of the flexible wire being bent in a U-shape so as to fit snugly within cap 125. The U-shaped end can be bonded to the cap 125 through the use of an adhesive. Cap 125 fits onto distal hub member 127 in a variety of manners, such as, by way of example, a snap fit or by threading onto distal hub member 127. Cap 125 can be selectively fit onto or removed from distal hub member 127. Furthermore, since the flexible wire is affixed to cap 125, the fitting of cap 125 onto distal hub member 127 inserts the flexible wire (not shown) into the secondary lumen of the cannula (not shown). Likewise, the removal of cap 125 from distal hub member 127 retracts the flexible wire from the secondary lumen of the cannula.

FIGS. 12B and 12C illustrate cross sectional diagrams of hub 122. FIG. 12B illustrates hub 122 in an extended position and FIG. 12C illustrates hub 122 in a contracted position. When hub 122 is in an extended position, the distal insertion end of the cannula can be extended so as to be in an extended position, and alternatively when hub 122 is in a contracted position, an anchoring configuration (i.e. a loop, j-curve, pigtail, malecot, etc.) is formed at the distal insertion end of the cannula.

As mentioned above, a cord can be used in a variety of manners to allow for the formation of an anchoring configuration to couple the catheter to the patient's body. By way of example, in FIGS. 12B and 12C the cord, labeled as cord 131, resembles a lasso, having a loop on a first end. The second end of cord 131 is fastened to hub 122 by use of a coupling means, such as pin 133, as described above in relation to FIG. 5A. Other examples of a coupling means include an insert molding, an adhesive, a snap ring, a C-clamp, or the like.

Tension on cord 131 can cause the cannula (not shown) to form an anchoring configuration at the distal insertion end of the cannula. The tension is placed on cord 131 by forcing cord 131 into channels 134, and is accomplished by pushing proximal hub member 128 toward distal hub member 127, thereby causing fingers 132 to push cord 131 into respective channels 134 (as illustrated in FIG. 12C).

Wire 135 extends into hub 122, down the secondary lumen of the cannula, and is used for securing cord 131 to the cannula to enable the formation of an anchoring configuration in the distal insertion end of the cannula. Upon removal or longitudinal displacement of cap 125 and wire 135, the looped end of cord 131 is released from wire 135. The releasing of the looped end of cord 131 releases the tension in cord 131, thereby allowing the drainage catheter to be decoupled from the patient's body by removing cannula 74 from the body, as will be further explained below.

Hubs 12, 72 and 122 disclosed above are each examples of a hub means coupled to the proximal end of a cannula for receiving fluid entering the distal insertion end of the cannula and for selectively tightening a cord upon movement of the hub means.

Employing a Cord at the Distal Insertion End of the Cannula

Another manner in which the present invention facilitates the coupling of a catheter to a patient's body and eases the decoupling of the catheter from the body regards the way in which the cord is threaded at the distal insertion end of the catheter cannula. As mentioned above, a cord is employed to cause an anchoring configuration to form at the distal insertion end of the cannula. FIGS. 13A–14B illustrate exemplary embodiments under the present invention for threading a cord to facilitate the decoupling of the cannula from the patient's body.

Figure 13B:
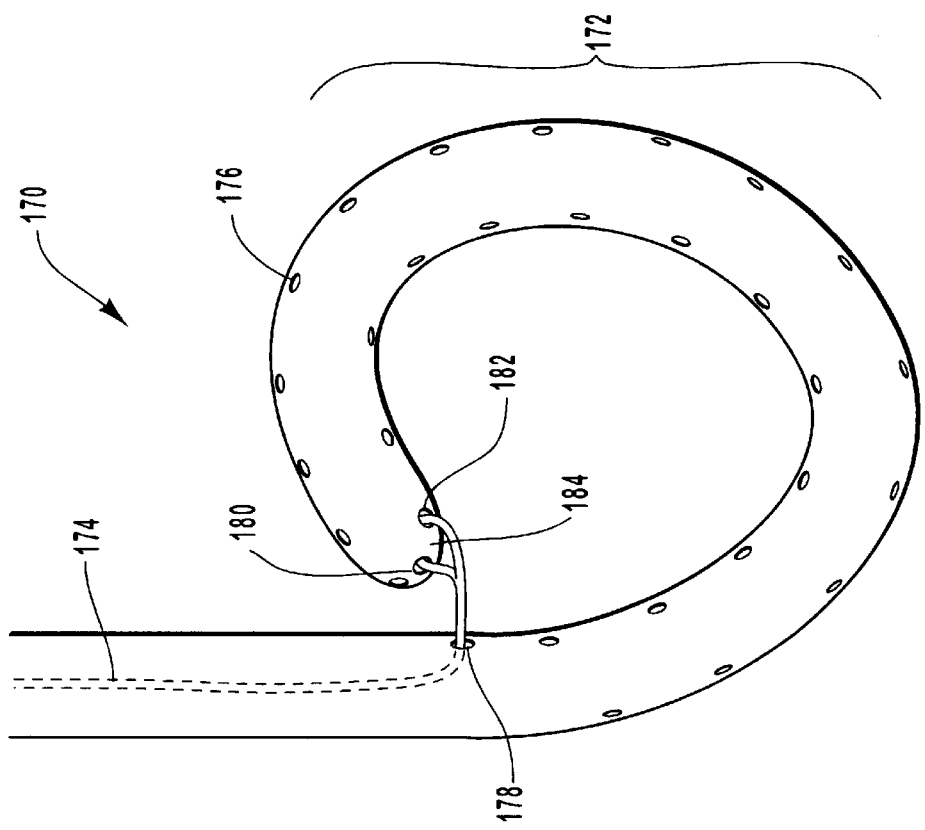
FIG. 13B illustrates another exemplary method for threading a cord to form a configuration that secures the distal insertion end to a patient as provided under an embodiment of the present invention.
Figure 13A:
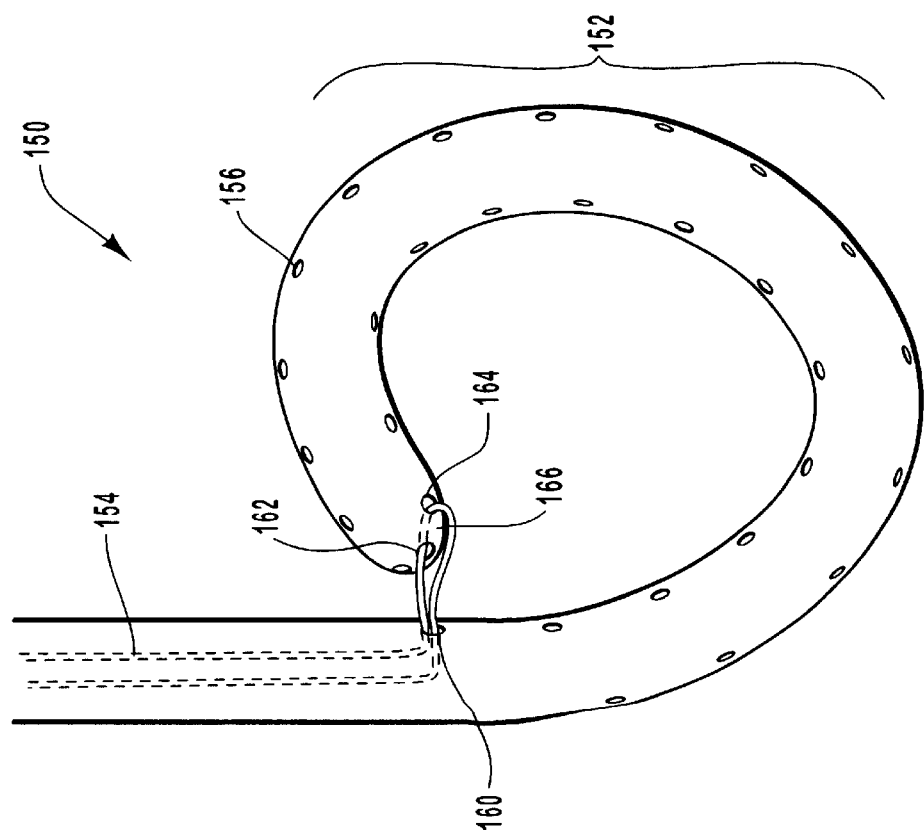
FIG. 13A illustrates an exemplary method for threading a cord to form an anchoring configuration that secures the distal insertion end of the catheter to a patient as provided under an embodiment of the present invention.

Referring first to FIG. 13A, an exemplary embodiment for threading the cord is illustrated, which can be used in connection with a variety of hub designs, such as those disclosed herein. In FIG. 13A, the distal insertion end of a catheter cannula is illustrated generally as cannula 150 and includes a plurality of fluid entrance openings, such as opening 156, to allow bodily fluid to enter cannula 150.

In one embodiment of the present invention, one end of cord 154 is affixed to the catheter hub and the other end extends along the hollow interior of the cannula, out a side opening such as opening 160, into the distal insertion end of cannula 150 through an opening such as opening 162, out of the distal insertion end of cannula 150 through an opening such as opening 164, back through a side opening such as opening 160 and is affixed to the catheter hub as explained in relation to FIG. 5 above. In one embodiment, openings 162 and 164 are spaced closely together.

A loop is formed in cannula 150 when the catheter hub is placed in a contracted position. As explained above, placing the hub in a contracted position causes cord 154 to be inserted into one or more channels, thereby shortening the amount of cord 154 in cannula 150 and causing an anchoring configuration, such as loop 152 to form. The hub may be locked into the contracted position while drainage takes place. During the period of drainage, the bodily fluid enters the drainage openings, such as opening 156, flows down cannula 150, through the catheter hub and out of the end of the hub or into a connector coupled thereto.

After the bodily fluid has drained, cannula 150 is decoupled from the patient's body. In one embodiment, the process of decoupling comprises relaxing cord 154 such that cannula 150 can be straightened and thus removed from the body. This may be accomplished, by way of example, by extending hub 12 into an extended position as illustrated in FIG. 2. In another embodiment, the process of decoupling according to an embodiment of the present invention includes pulling cord 154 of FIG. 13A. The pulling causes the portion of the cannula between openings 162 and 164, illustrated as cannula portion 166, to tear away. With cannula portion 166 torn way, cord 154 is released from the distal insertion end of cannula 150. Therefore, upon pulling on the catheter, cannula 150 can be slid out of the body to decouple the catheter from the patient's body. Alternatively, cord 154 could be cut to allow for the removal of the catheter from the body.

Referring next to FIG. 13B, another exemplary embodiment is illustrated, which can be used in connection with a variety of hub designs, such as those disclosed herein. In FIG. 13B, catheter cannula, illustrated generally as cannula 170, includes a plurality of fluid entrance openings, such as opening 176, to allow bodily fluid to enter cannula 170. Cord 174 resembles a lasso having a loop at one end. The non-looped end of cord 174 is affixed to the catheter hub and the looped end extends through the cannula, out a side opening such as opening 178, and is attached to the distal insertion end of cannula 170 by entering openings 180 and 182, thereby surrounding distal cannula portion 184. In one embodiment openings 180 and 182 are spaced closely together.

A loop is formed in cannula 170 under embodiments of the present invention when the catheter hub is placed in a contracted position. As explained above, placing the hub in a contracted position causes cord 174 to be inserted into one or more channels, thereby shortening the amount of the cord in cannula 170 and causing an anchoring configuration, such as loop 172 to form. The hub can be locked into the contracted position while drainage takes place. During the period of drainage, the bodily fluid enters the fluid entrance openings, such as opening 176, runs down cannula 170, through the catheter hub and out the proximal end of the catheter.

After the bodily fluid has drained, cannula 170 is decoupled from the patient's body. In a similar manner as explained above, the process of decoupling can include pulling cord 174. The pulling causes distal cannula portion 184 to tear away, thereby releasing cord 174 from the distal insertion end of cannula 170. With cord 174 no longer attached to the distal insertion end of cannula 170, the catheter can be decoupled from the patient's body. Upon pulling the catheter, cannula 170 can be slid out of the body, thereby decoupling the catheter from the patient's body. Alternatively, cord 174 could be cut to allow for the removal of the catheter from the body.

Figure 13C:
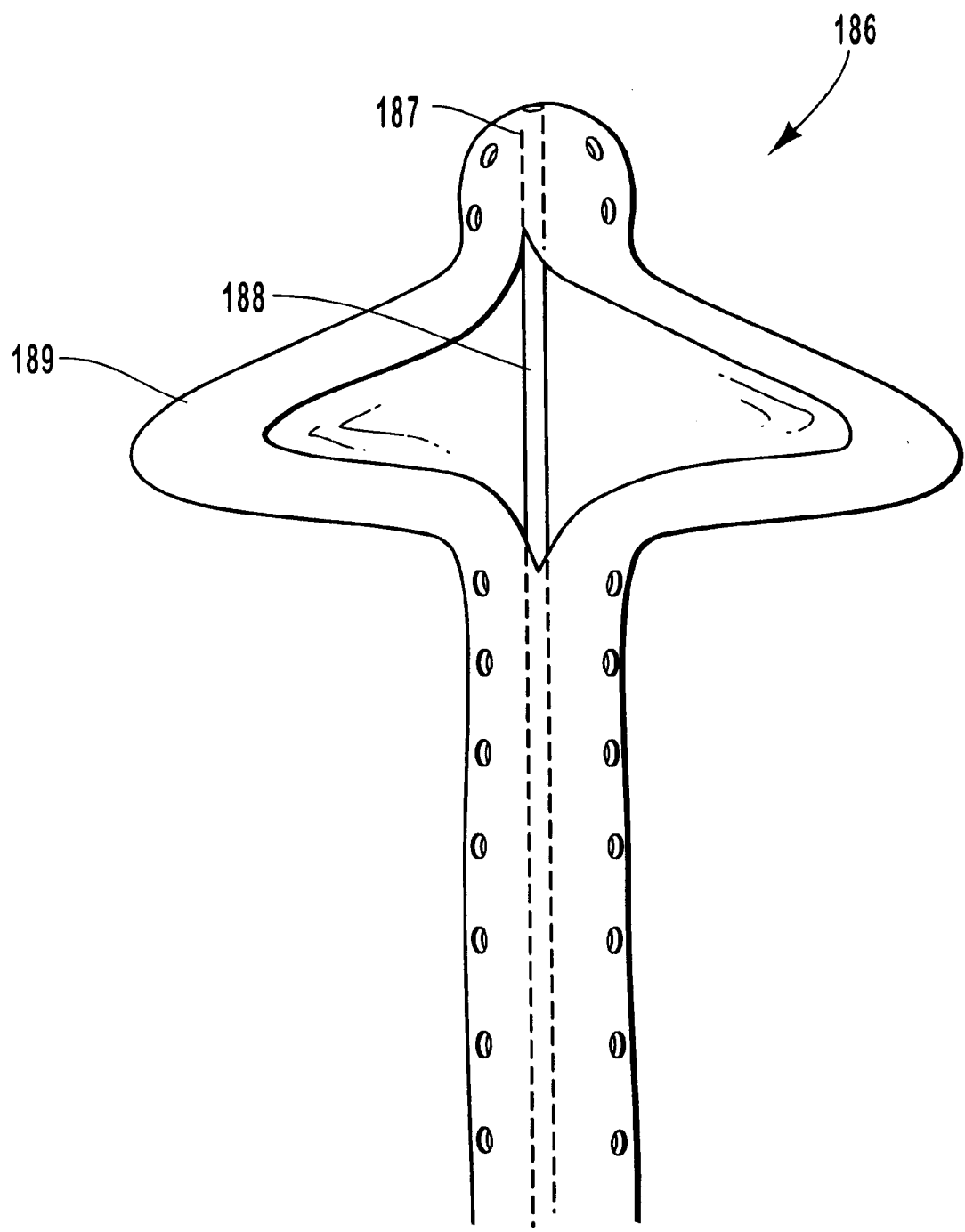
FIG. 13C illustrates another exemplary configuration for securing the distal insertion end to a patient as provided under an embodiment of the present invention.

As explained above, when the hub is placed in a contracted position the cord is inserted into one or more channels, causing tension on the cord, and an anchoring configuration is formed at or near the distal end of the cannula. By way of example, the configuration formed can include a loop, pigtail, j-curve, malecot, and so forth. FIG. 13C illustrates the formation of a malecot configuration, referred to generally as malecot 186. In the illustrated embodiment, a first end of cord 188 is affixed to the hub and a second end of cord 188 is affixed to distal cannula tip 187. The configuration is formed when the hub is placed into a contracted position that creates tension in cord 188 and pulls distal cannula tip 187 toward the hub. The movement of the distal cannula tip toward the hub causes one or more wings to be formed, such as wing 189. The one or more wings prevent the cannula from being removed from the patient's body, thereby coupling the catheter to the body. To decouple the catheter from the body, the hub is placed back into an extended position to eliminate the tension in cord 188 and to allow the cannula to straighten so that it can be removed from the patient's body.

Figure 14B:
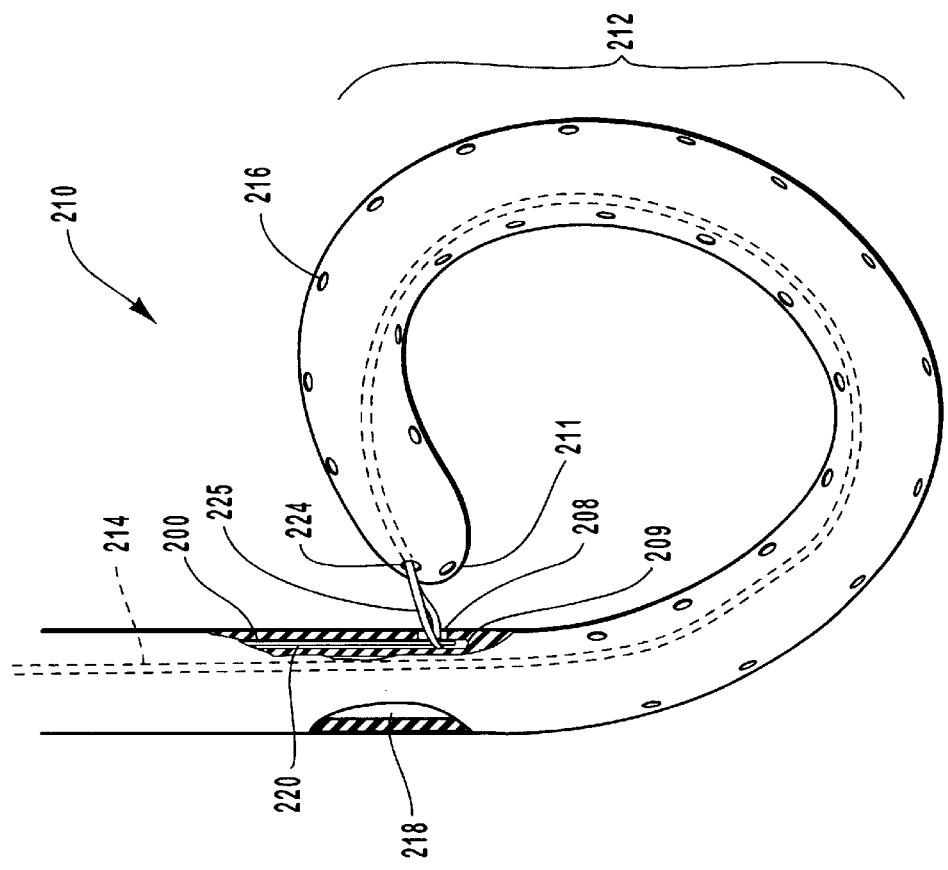
FIG. 14B illustrates another exemplary method for threading a cord around a wire to form a configuration that secures the distal insertion end to a patient as provided under an embodiment of the present invention.
Figure 14A:
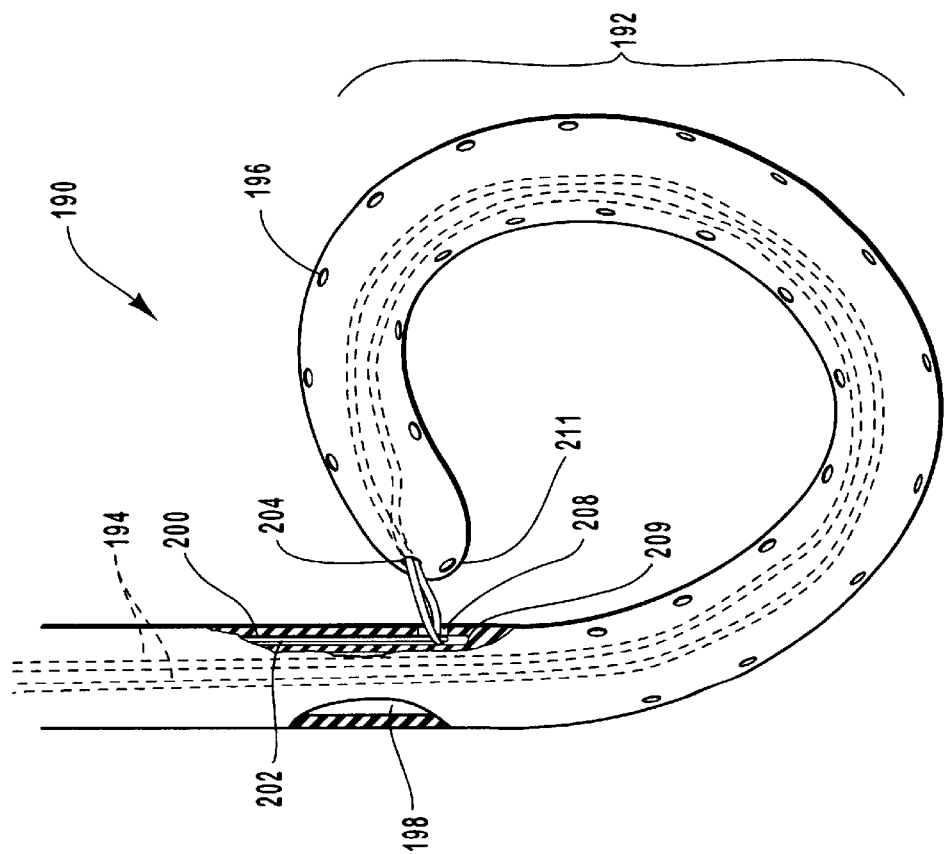
FIG. 14A illustrates an exemplary method for threading a cord around a wire to form a configuration that secures the distal insertion end to a patient as provided under an embodiment of the present invention.

Referring now to FIG. 14A, an exemplary embodiment is illustrated for threading a cord that can be used in connection with any of the hub designs disclosed herein that employ a flexible wire. In FIG. 14A, the distal portion of a catheter cannula is illustrated generally as cannula 190 and includes primary and secondary lumens, the primary lumen configured to receive fluid flowing therethrough and the secondary lumen configured to receive a flexible wire there through. Cannula 190 also includes a plurality of fluid entrance openings, such as opening 196, to allow bodily fluid to enter cannula 190. Under the illustrated embodiment, a first end of cord 194 is affixed to the catheter hub and the other end extends down primary lumen 198 of cannula 190, exists cannula 190 through an opening, such as opening 204, enters the secondary lumen 200 through opening 208, wraps around the flexible wire, such as wire 202, exits secondary lumen 200 through opening 208, re-enters primary lumen 198 through opening 204, extends down primary lumen 198 of cannula 190 and is affixed to the hub.

In an alternative embodiment, the wire and the cord extend down the same lumen. Under one such alternative embodiment, secondary lumen 200 extends down to or near distal tip portion 211 of cannula 190. A first end of the cord is affixed to the catheter hub and the other end extends down secondary lumen 200, exits cannula 190 through an opening at or near distal tip portion 211, re-enters secondary lumen 200 through an opening such as opening 208, wraps around wire 202, exits secondary lumen 200 through opening 208, re-enters secondary lumen 200 through an opening at or near distal tip portion 211, extends down secondary lumen 200 of cannula 190 and is affixed to the catheter hub.

Referring to the embodiment illustrated in FIG. 14A, wire 202 is used to secure cord 194 and can be made of a variety of materials, such as nitinol, stainless steel, plastic, or another material or combination of materials to allow wire 202 to have the strength necessary to secure cord 194 and the flexibility necessary to allow the catheter to bend.

Cannula 190 is an example of cannula means for defining a primary lumen and a secondary lumen. In yet another embodiment, however, the cannula includes only one lumen and the flexible wire extends down the lumen. Nevertheless, in accordance with the preferred embodiment, the cannula includes a plurality of lumens, such as, by way of example, a primary lumen and a secondary lumen, with the flexible wire extending down the secondary lumen.

Under the embodiments in which the cannula includes a primary lumen and a secondary lumen and the primary lumen is configured to receive fluid flowing therethrough and the secondary lumen is configured to receive a flexible wire therethrough, the diameter of the primary lumen can be large to allow for greater flow of the bodily liquid while the diameter of the secondary lumen can be smaller to accommodate the flexible wire.

In another embodiment, two cannulas, each having a separate lumen, are affixed in a parallel fashion with each other, one cannula configured to receive flowing liquid, the other configured to received the wire. This embodiment is another example of cannula means for defining a primary lumen and a secondary lumen. However, the use of one cannula having a plurality of lumens is preferred, as it facilitates the insertion of the catheter into the patient's body. The embodiment illustrated in FIG. 14A includes primary lumen 198, secondary lumen 200, and wire 202, made, by way of example, of nitinol, which extends down secondary lumen 200.

An anchoring configuration is formed in cannula 190 under the present invention when the hub is placed in a contracted position. As explained above, placing the hub into a contracted position causes cord 194 to be inserted into one or more channels within the hub, thereby shortening the amount of cord in cannula 190 and causing loop 192 to form. The hub can be locked in the contracted position while drainage takes place. During the period of drainage, the bodily fluid enters the fluid entrance openings, such as opening 196, drains down the cannula, through the catheter hub and out the proximal end of the catheter.

The process of decoupling the catheter from the patient's body, according to the embodiment illustrated in FIG. 14A, includes removing or displacing wire 202 so that cord 194 is no longer wrapped around wire 202. The removal of wire 202 takes place, by way of example, upon removing cap 85 of FIG. 8, to which wire 202 can be attached, and pulling wire 202 out of secondary lumen 200. Alternatively, the displacement of wire 202 includes removing the cap and then retracting wire 202 from cord 194. The removal or displacement of wire 202 releases cord 194 and allows cannula 190 to slide out of the patient's body upon pulling on the catheter. Alternatively, cord 194 can be cut to release cord 194 from wire 202 to allow for the removal of cannula 190. Releasing cord 194 eliminates the tension in cord 194 and thereby eliminates the possibility of cord 194 being tight and slicing through the patient's bodily tissue. The removal of cannula 190 decouples the catheter from the patient's body.

Referring next to FIG. 14B, another embodiment is illustrated for threading a cord that can be used in connection with any of the hub designs disclosed herein that employ a flexible cord or wire. In FIG. 14B, cannula 210 includes primary and secondary lumens. Cannula 210 is another example of cannula means for defining a primary lumen and a secondary lumen. The primary lumen is configured to receive fluid flowing therethrough and the secondary lumen is configured to receive a wire therethrough. Cannula 210 further includes a plurality of fluid entrance openings, such as opening 216, to allow bodily fluid to enter the cannula. The illustrated embodiment includes a cord that has a loop, illustrated as loop 225, at one end. The non-looped end of cord 214 is affixed to the catheter hub and the looped end extends down primary lumen 218, out opening 224, and into secondary lumen 200. A flexible wire, such as wire 220, extends through the loop in cord 214, thereby securing the cord.

In an alternative embodiment, the wire and cord extend down the same lumen. Under one such alternative embodiment, the secondary lumen 200 extends down to or near distal tip portion 211 of cannula 210. A non-looped end of the cord is affixed to the catheter hub and the looped end extends down secondary lumen 200, exits secondary lumen 200 through an opening at or near distal tip portion 211, and re-enters secondary lumen 200 through opening 208. A flexible wire extends through the loop to secure the cord.

Wire 220 is used to secure cord 214 and can be made of a variety of materials, such as nitinol, stainless steel, plastic, or another material or combination of materials to allow wire 220 to have the strength necessary to secure cord 214 and the flexibility necessary to allow the catheter to bend.

An anchoring configuration, such as loop 212, is formed in cannula 210 under the present invention when the catheter hub is placed in a contracted position. As explained above, placing the hub in a contracted position causes cord 214 to be inserted into one or more channels within the hub, thereby shortening the amount of cord in cannula 210 and causing the formation of an anchoring configuration, such as loop 212. The hub is locked into the contracted position while drainage takes place. During the period of drainage, the bodily fluid enters fluid entrance openings, such as opening 216, flows down cannula 210, through the catheter hub and out the proximal end of the catheter.

After the bodily fluid has drained, cannula 150 is decoupled from the patient's body. The process of decoupling according to the embodiment illustrated in FIG. 14B includes removing wire 220 from lumen 200 or displacing it longitudinally away from cord 214. Alternatively, cord 214 can be cut to release cord 214 from wire 220 to allow for the removal of cannula 190. The removal of wire 220 releases cord 214 and allows for cannula 210 to be slid out of the body upon pulling on the catheter. Releasing cord 214 eliminates the tension in cord 214 and thereby eliminates the possibility of cord 214 being tight and slicing through the patient's bodily tissue. The removal of cannula 201 decouples the catheter from the patient's body.

As one advantage of the primary and secondary lumens shown and referred to in FIGS. 7, 8, 10, 11, 12B, 12C, 14A and 14B, the lumens are separate and distinct, rather than having an opening which connects the lumens in fluid communication. Thus, primary lumen 198 is separate and distinct from secondary lumen 200, for example. Consequently, fluid flowing through primary lumen 198 does not flow into secondary lumen 200. Thus, secondary lumen 200 does not become filled with fluid flowing from primary lumen 198. This prevents fluid from primary lumen 198 from encrusting secondary lumen 200, which could clog secondary lumen 200 and prevent a wire 202 from being removed therefrom.

As another advantage, in one embodiment, the secondary lumen, e.g., secondary lumen 200, has a first open end, in which a wire is initially placed, and a second closed end 209, as shown in FIG. 14A. Since the second end 209 is closed, fluid does not flow into the second end 209, preventing the second end 209 from becoming encrusted and reducing the amount of fluid in the secondary lumen.

As another advantage of the embodiments shown and referred to in FIGS. 7, 8, 10, 11, 12B, 12C, 14A and 14B, the cord, e.g., cord 194 (FIG. 14A) extends along the distal insertion end of the cannula and extends out of a distal tip portion, e.g., distal tip portion 211 (FIG. 14A), of the distal insertion end of the cannula. Thus, cord 194 extends along the anchoring configuration (e.g., loop 192) when the cord is tightened. Since cord 194 extends along the anchoring configuration, wire 202 can be straight within the distal portion of the secondary lumen, rather than being required to curve through the anchoring configuration. This can make tightening more convenient because the practitioner is not required to bend the wire. Furthermore, the amount of cord 194 extending out of the distal insertion end is minimal, reducing potential encrustation and possible injury to the patient.

Optionally, however, the cord extends from another portion other than the distal tip portion, e.g., from a portion of the cannula preceding the anchoring configuration. Furthermore, in another embodiment, the wire can be configured to curve through the anchoring configuration.

A variety of different cannula means for defining a primary lumen and a secondary lumen are available for use in the present invention, such as those disclosed herein or any other structure having a first lumen and a second lumen.

According to the present invention, the processes of coupling a catheter to a patient's body and decoupling the catheter from the body are facilitated, by way of example, according to the description of the embodiments provided above. The present invention may also be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. In a catheter system adapted for draining undesired body fluid from a body cavity of a patient, a drainage catheter that facilitates secure placement and anchoring within the desired body cavity and subsequent release to facilitate removal of the catheter when desired, comprising:
   a flexible cannula comprising an insertion end that includes at least one drainage opening for placement within a body cavity of a patient to permit drainage of undesired body fluids in the body cavity, and a connection end that terminates outside the patient's body, the flexible cannula further comprising
      a primary lumen extending through the entire length of the flexible cannula, and
      a secondary lumen extending from the connection end of the flexible cannula and along at least a portion of the length of the primary lumen;
   a cord extending from the connection end of said flexible cannula and running through the primary lumen to a point that is beyond the length of the secondary lumen;
   a wire placed within said secondary lumen, and comprising
      a first end over which the cord is secured for purposes of permitting the cord to be used to form the insertion end of the flexible cannula into an anchoring configuration once placed within the body cavity of the patient, and
      a second end which terminates outside of the patient's body so that said second end is grasped and pulled to effect release of the secured cord to thereby release the flexible cannula from the anchoring configuration when removal of the insertion end of the flexible cannula from the body cavity is desired; and a hub mechanism joined to the connection end of the flexible cannula, and comprising
      a channel that communicates with said primary lumen to permit fluid drainage therethrough,
      means for tightening the cord when said means for tightening is secured over said first end of said wire, said means for tightening the cord being operable to move from a first position in which the cord is not tightened to a second position in which the cord is tightened so as to place the insertion end of the flexible cannula into said anchoring configuration, and
      locking means for selectively locking the means for tightening into said second position, such that subsequent release of the anchoring configuration is effected only by pulling said wire to effect release of the secured cord over the wire.

2. A drainage catheter as defined in claim 1 wherein said means for tightening the cord comprises first and second hub members slidably joined with one another so as to be operable to slide from a first position in which the cord is not tightened to a second position in which the cord is tightened so as to place the insertion end of the flexible cannula into said anchoring configuration.

3. A drainage catheter as defined in claim 1 wherein said hub mechanism further comprises a side port having a lumen that communicates with second secondary lumen of the flexible cannula.

4. A drainage catheter as defined in claim 3 wherein said wire runs through the lumen of said side port and said secondary lumen.

5. A drainage catheter as defined in claim 4 further comprising a cap which is attached to said wire, so that when the cap is placed over said side port, the wire is fully positioned within said secondary lumen or the flexible cannula so as to secure said cord at said one end of the wire, and so that when the cap is removed from the side port, the cord is released from said one of the wire as the wire is withdrawn from said secondary lumen, thereby releasing the insertion end of the flexible cannula from the anchoring configuration.

6. In a catheter system adapted for draining undesired body fluid from a body cavity of a patient, a drainage catheter that facilitates secure placement and anchoring within the desired body cavity and subsequent release to facilitate removal of the catheter when desired, comprising:
- a flexible cannula comprising an insertion end that includes at least one drainage opening for placement within a body cavity of a patient to permit drainage of undesired body fluids in the body cavity, and a connection end that terminates outside the patient's body, the flexible cannula further comprising
  - a primary lumen extending through the entire length of the flexible cannula, and
  - a secondary lumen extending from the connection end of the flexible cannula and along at least a portion of the length of the primary lumen;
- a cord extending from the connection end of said flexible cannula and running through the primary lumen to a point that is beyond the length of the secondary lumen;
- a wire placed within said secondary lumen, and comprising
  - a first end over which the cord is secured for purposes of permitting the cord to be used to form the insertion end of the flexible cannula into an anchoring configuration once placed within the body cavity of the patient, and
  - a second end which terminates outside of the patient's body so that said second end is grasped and pulled to effect release of the secured cord to thereby release the flexible cannula from the anchoring configuration when removal of the insertion end of the flexible cannula from the body cavity is desired; and
- a hub mechanism joined to the connection end of the flexible cannula, and comprising
  - a channel that communicates with said primary lumen to permit fluid drainage therethrough,
  - first and second hub members slidably joined with one another so as to be operable to slide from a first position in which the cord is not tightened to a second position in which the cord is tightened so as to place the insertion end of the flexible cannula into said anchoring configuration, and
  - locking means for selectively locking the first and second hub members into said second position, such that subsequent release of the anchoring configuration is effected only by pulling said wire to effect release of the secured cord over the wire.

7. A drainage catheter as defined in claim 6 wherein said channel of the hub mechanism is formed so as to run through both said first and said members.

8. A drainage catheter as defined in claim 7 wherein said first position is provided when the first and second slidable hub members are extended away from one another.

9. A drainage catheter as defined in claim 8 wherein said second position is provided when the first and second slidable hub members are slid together.

10. A drainage catheter as defined in claim 9 wherein said locking means for selectively locking the first and second hub members into said second position comprises a protusion formed on one of said first and second hub members, and book formed on the other of said first and second hub member, so that the protusion and hook catch one another when the first and second hub members are slid together into said second position.

11. A drainage catheter as defined in claim 9 wherein said first and second hub members comprise at least one finger formed on one of said first and second hub members, and at least one corresponding channel for receiving said finger, formed on the other of said first and second hub members, so that said finger slides into said corresponding channel for receiving said finger as the first and second hub members slide together into said second position.

12. A drainage catheter as defined in claim 11 wherein said cord is positioned around said finger so that as the first and second hub members slide together into said second position, the cord is tightened as the finger slides into the corresponding channel for receiving the finger.

13. A drainage catheter as defined in claim 7 or 12 wherein said hub mechanism further comprises a side port having a lumen that communicates with second secondary lumen of the flexible cannula.

14. A drainage catheter as defined in claim 13 wherein said wire runs through the lumen of said side port and said secondary lumen.

15. A drainage catheter as defined in claim 14 further comprising a cap which is attached to said wire, so that when the cap is placed over said side port, the wire is fully positioned within said secondary lumen of the flexible cannula so as to secure said cord at said one end of the wire, and so that when the cap is removed from the side port, the cord is released from said one of the wire as the wire is withdrawn from said secondary lumen, thereby releasing the insertion end of the flexible cannula from the anchoring configuration.

* * * * *

UNITED STATES PATENT AND TRADEMARK OFFICE
CERTIFICATE OF CORRECTION

PATENT NO.     : 6,508,789 B1
DATED          : January 21, 2003
INVENTOR(S)    : Sinnot et al.

It is certified that error appears in the above-identified patent and that said Letters Patent is hereby corrected as shown below:

Column 15,
Line 54, after "other configured to" please delete "received" and insert -- receive --

Column 19,
Line 4, after "said secondary lumen" please delete "or" and insert -- of --

Column 20,
Line 19, before "formed on the other" please delete "book" and insert -- hook --
Line 35, after "as defined in" please delete "claim" and insert -- claims --

Signed and Sealed this

Sixth Day of January, 2004

JAMES E. ROGAN
*Director of the United States Patent and Trademark Office*